United States Patent
Rajan

(10) Patent No.: US 11,124,783 B2
(45) Date of Patent: Sep. 21, 2021

(54) VARIANT CAS9 PROTEINS WITH IMPROVED DNA CLEAVAGE SELECTIVITY

(71) Applicant: The Board of Regents of the University of Oklahoma, Norman, OK (US)

(72) Inventor: Rakhi Rajan, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/570,555

(22) Filed: Sep. 13, 2019

(65) Prior Publication Data

US 2020/0087639 A1    Mar. 19, 2020

Related U.S. Application Data

(60) Provisional application No. 62/730,890, filed on Sep. 13, 2018.

(51) Int. Cl.
 *C12N 9/22*   (2006.01)
 *C12N 15/11*  (2006.01)
 *C12N 15/70*  (2006.01)

(52) U.S. Cl.
 CPC ............... *C12N 9/22* (2013.01); *C12N 15/11* (2013.01); *C12N 15/70* (2013.01); *C12N 2310/20* (2017.05); *C12N 2800/80* (2013.01)

(58) Field of Classification Search
 CPC .......... C12N 9/22; C12N 15/11; C12N 15/70; C12N 2310/20; C12N 2800/80; C12N 15/102

See application file for complete search history.

(56) References Cited

PUBLICATIONS

Mali et al. RNA-Guided Human Genome Engineering via Cas9. Science (2013), 339: 823-826.*
Rasmussen et al. Whole genome sequencing as a tool for phylogenetic analysis of clinical strains of Mitis group streptococci. Eur J Clin Microbiol Infect Dis (2016) 35:1615-1625.*
UniProt accession No. A0A1X1JP06, CRISPR-associated endonuclease Cas9, created on Jul. 5, 2017.*
Gaudelli, N.M., et al.; "Programmable base editing of A-T to G-C in genomic DNA without DNA cleavage"; Nature 551:7681 (2017) 37 pages.
Hess, G.T., et al.; "Methods and Applications of CRISPR-Mediated Base Editing in Eukaryotic Genomes"; Molecular Cell 68 (2017) 26-43.
Huai, C., et al.; "Structural insights into DNA cleavage activation of CRISPR-Cas9 system"; Nature Communications 8:1375 (2017) 10 pages.
Koonin, E.V., et al.; "Diversity, classification and evolution of CRISPR-Cas systems"; Current Opinion in Microbiology 37 (2017) 67-78.
Ma, H., et al.; "Correction of a pathogenic gene mutation in human embryos"; Nature 548 (2017) 24 pages.
Shmakov, S., et al.; "Diversity and evolution of class 2 CRISPR-Cas systems"; Nature Reviews; Microbiology 15 (2017) 169-182.
Swarts, D.C., et al.; "Structural Basis for Guide RNA Processing and Seed-Dependent DNA Targeting by CRISPR-Cas 12a"; Molecular Cell 66 (2017) 221-233.
Vriend, L.E.M., et al.; "Nick-initiated homologous recombination: Protecting the genome, one strand at a time"; DNA Repair 50 (2017) 1-13.
Wang, Q. et al.; "Genome modification of CXCR4 by *Staphylococcus aureus* Cas9 renders cells resistance to HIV-1 infection"; Retrovirology 14:51 (2017) 12 pages.
Yamada, M., et al.; "Crystal Structure of the Minimal Cas9 from Campylobacter jejuni Reveals the Molecular Diversity in the CRISPR-Cas9 systems"; Molecular Cell 65 (2017) 1109-1121.
Amrani, N., et al.; "NmeCas9 is an intrinsically high-fidelity genome-editing platform"; Genome Bioloty 19:214 (2018) 25 pages.
Gao, X.D., et al.; "C-BERST: defining subnuclear proteomic landscapes at genomic elements with dCas9-APEX2"; Nature Methods 15 (2018) 433-436.
Yang, M., et al.; "The Conformational Dynamics of Cas9 Governing DNA Cleavage Are Revealed by Single-Molecule FRET"; Cell Reports 22 (2018) 372-382.
Zeng, Y., et al.; "The initiation, propagation and dynamics of CRISPR-SpyCas9 R-loop complex"; Nucleic Acids Research 46:1 (2018) 350-361.
Calnan, B.J., et al.; "Analysis of arginine-rich peptides from the HIV Tat protein reveals unusual features of RNA-protein recognition"; Genes & Development 5 (1991) 201-210.
Ihaka, R., et al.; "R: A Language for Data Analysis and Graphics"; Journal of Computational and Graphical Statistics 5:3 (1996) 299-314.
Weiss, M.A., et al.; "RNA Recognition by Arginine-Rich Peptide Motifs"; Bioploymers (Nucleic Acid Sciences) 48 (1998) 167-180.
DeLano, W.L.; "PyMOL: An Open-Source Molecular Graphics Tool"; DeLano Scientific (2002) 9 pages.
Barrangou, R., et al.; "CRISPR Provides Acquired Resistance Against Viruses in Prokaryotes"; Science 315:5819 (2007) 1709-1712.
Brouns, J.J., et al.; "Small CRISPR RNAs Guide Antiviral Defense in Prokaryotes"; Science 321:5891 (2008) 960-964.
Deveau, H., et al.; "Phage Response to CRISPR-Encoded Resistance in *Streptococcus thermophilus*"; Journal of Bacteriology 190:4 (2008) 1390-1400.
Edelheit, O., et al.; "Simple and efficient site-directed mutagenesis using two single-primer reactions in parallel to generate mutants for protein structure-function studies"; BMC Biotechnology 9:61 (2009) 8 pages.
Gibson, D.G., et al.; "Enzymatic assembly of DNA molecules up to several hundred kilobas1"; Nature Methods 6:5 (2009) 343-347.

(Continued)

*Primary Examiner* — Iqbal H Chowdhury
(74) *Attorney, Agent, or Firm* — Hall Estill Law Firm

(57) ABSTRACT

Bridge helix-modified variant Cas9 proteins having improved DNA cleavage selectivity in comparison to wild type versions of the Cas9 proteins, nucleic acids encoding the variant proteins, host cells containing the nucleic acids, and methods of their use.

9 Claims, 9 Drawing Sheets

Specification includes a Sequence Listing.

(56) References Cited

PUBLICATIONS

Hale, C.R., et al.; "RNA-Guided RNA Cleavage by a CRISPR RNA-Cas Protein Complex"; Cell 139 (2009) 945-956.

Marraffini, L.A., et al.; "Invasive DNA, Chopped and in the CRISPR"; Structure 17 (2009) 786-788.

Garneau, J.E., et al.; "The CRISPR/Cas bacterial immune system cleaves bacteriophage and plasmid DNA"; Nature 468 (2010) 6 pages.

Marraffini, L.A., et al.; "CRISPR interference: RNA-directed adaptive immunity in bacteria and archaea"; Nature Reviews; Genetics 11 (2010) 11 pages.

Marraffini, L.A., et al.; "Self versus non-self discrimination during CRISPR RNA-directed immunity"; Nature 463 (2010) 5 pages.

Gasiumas, G., et al.; "Cas9-crRNA ribonucleoprotein complex mediates specific DNA cleavage for adaptive immunity in bacteria"; PNAS (2012) 8 pages.

Jinek, M., et al.; "A Programmable Dual-RNA-Guided DNA Endonuclease in Adaptive Bacterial Immunity"; Science 337:6096 (2012) 816-821.

Schneider, C.A., et al.; "NIH Image to ImageJ: 25 years of image analysis"; Nature Methods 9:7 (2012) 671-675.

Bachman, J.; "Site-Directed Mutagenesis"; Methods in Enzymology 529 (2013) 241-248.

Casu, F. et al.; "The Arginine-Rich RNA-Binding Motif of HIV-1 Rev Is Intrinsically Disordered and Folds upon RRE Binding"; Biophycial Journal 105 (2013) 1004-1017.

Hou, Z., et al.; "Efficient genome engineering in human pluripotent stem cells using Cas9 from Neisseria memingfils"; National Academy of Sciences 110-39 (2013) 15644-15649.

Mali, P., et al.; "CAS9 transcriptional activators for target specificity screening and paired nickases for cooperative genome engineering"; Nat Biotechnol. 31:9 (2013) 833-838.

Pennisi, E.; "The CRISPR Craze"; Science 341:6148 (2013) 833-836.

Sampson, T.R., et al.; "Corrigendum: A CRISPR/Cas system mediates bacterial innate immune evasion and virulence"; Nature 501 (2013) 262.

Scholz, J., et al.; "A new method to customize protein expression vectors for fast, efficient and background free parallel cloning"; BMC Biotechnology 13:12 (2013) 12 pages.

Anders, C., et al.; "Structural basis of PAM-dependent target DNA recognition by the Cas9 endonuclease"; Nature 513 (2014) 17 pages.

Brinkman, E.K., et al.; "Easy quantitative assessment of genome editing by sequence trace decomposition"; Nucleic Acids Research 42:22 (2014) 8 pages.

Doudna, J.A., et al.; "Methods in Enzymology. The use of CRISPR/Cas9, ZFNs, and TALENs in generating site-specific genome alternations. Preface. Methods Enzymol"; (2014) xix-xx.

Jinek, M., et al.; "Structures of Cas9 Endonucleases Reveal RNA-Mediated Conformational Activation"; Science 343:6176 (2014) 1215.

Kearns, N.A., et al.; "Cas9 effector-mediated regulation of transcription and differentiation in human pluripotent stem cells"; Development 141 (2014) 219-223.

Nishimasu, H., et al.; "Crystal Structure of Cas9 in Complex with Guide RNA and Target DNA"; Cell 156 (2014) 935-949.

Sternberg, S.H., et al.; "DNA interrogation by the CRISPR RNA-guided endonuclease Cas9"; Nature 507 (2014) 18 pages.

Szczelkun, M.D., et al.; "Direct observation of R-loop formation by single RNA-guided Cas9 and Cascade effector complexes"; National Academy of Sciences 111:27 (2014) 9798-9803.

Tsai, S.Q. et al.; "Dimeric CRISPR RNA-guided FokI nucleases for highly specific genome editing"; Nature Biotechnology 32:6 (2014) 569-576.

Zhou, Y., et al.; "High-throughput screening of a CRISPR/Cas9 library for functional genomics in human cells"; Nature 509 (2014) 487-491.

Bolukbasi, M.F., et al.; "DNA-biding-domain fusions enhance the targeting range and precision of Cas9"; Nature Methods 12:12 (2015) 16 pages.

Xiao-Jie, L., et al.; "CRISPR-Cas9: a new and promising player in gene therapy"; J Med Genet 52 (2015) 289-296.

Doudna, J.A.; Genomic Engineering and the Future of Medicine; JAMA 313:8 (2015) 791-792.

Nishimasu, H., et al.; "Crystal Structure of *Staphylococcus aureus* Cas 9"; Cell 162 (2015) 1113-1126.

Sternberg, S.H., et al.; "Conformational control of DNA target cleavage by CRISPR-Cas9"; Nature 527 (2015) 15 pages.

Tsai, S.Q. et al.; "GUIDE-Seq enables genome-wide profiling of off-target cleavage by CRISPR-Cas nucleases"; Nat Biotechnol. 33:2 (2015) 187-197.

Abudayyeh, O.O., et al.; "C2c2 is a single-component programmable RNA-guided RNA-targeting CRISPR effector"; Science 353:6299 (2016) 557; 11 pages.

Hirano, H., et al.; "Structure and Engineering of Francisella novicida Cas9"; Cell 164 (2016) 950-961.

Jiang, F., et al.; "Structures of a CRISPR-Cas9 R-loop complex primed for DNA cleavage"; Science 351:6275 (2016) 9 pages.

Kleinstiver, B.P., et al.; "High-fidelity CRISPR-Cas9 nucleases with no detectable genome-wide off-target effects"; Nature 529 (2016) 36 pages.

Mohanraju, P., et al.; "Diverse evolutionary roots and mechanistic variations of the CRISPR-Cas systems"; Science 353:6299 (2016) 14 pages.

Singh, D., et al.; "Real-time observation of DNA recognition and rejection by the RNA-guided endonuclease Cas9"; Nature Communications (2016) 9 pages.

Slaymaker, I.M., et al.; "Rationally engineered Cas9 nucleases with improved specificity"; Science 351:6268 (2016) 6 pages.

Yang, H.Y., et al.; "PAM-Dependent Target DNA Recognition and Cleavage by C2c1 CRISPR-Cas Endonuclease"; Cell 167 (2016) 1814-1828.

Chen, J.S., et al.; "Enhanced proofreading governs CRISPR-Cas9 targeting accuracy"; Nature 550:7676 (2017) 25 pages.

Fogarty, N.M.E., et al.; "Genome editing reveals a role for OCT4 in human embryogenesis"; Nature (2017) 25 pages.

\* cited by examiner

SEQUENCE LISTING

<160> NUMBER OF SEQ ID NOS: 10

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
    675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
    755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
```

```
           785                 790                 795                 800
Val Glu Asn Thr Gln Leu Gln Asn Gly Lys Leu Tyr Leu Tyr Tyr Leu
                    805                 810                 815
Gln Asn Gly Arg Asp Met Tyr Val Asp Gln Glu Leu Asp Ile Asn Arg
                    820                 825                 830
Leu Ser Asp Tyr Asp Val Asp His Ile Val Pro Gln Ser Phe Leu Lys
                    835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                    885                 890                 895
Phe Asp Asn Leu Thr Lys Ala Glu Arg Gly Gly Leu Ser Glu Leu Asp
                    900                 905                 910
Lys Ala Gly Phe Ile Lys Arg Gln Leu Val Glu Thr Arg Gln Ile Thr
                    915                 920                 925
Lys His Val Ala Gln Ile Leu Asp Ser Arg Met Asn Thr Lys Tyr Asp
                    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                    965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
                    995                 1000                1005
Val Tyr Gly Asp Tyr Lys Val Tyr Asp Val Arg Lys Met Ile Ala
                    1010                1015                1020
Lys Ser Glu Gln Glu Ile Gly Lys Ala Thr Ala Lys Tyr Phe Phe
                    1025                1030                1035
Tyr Ser Asn Ile Met Asn Phe Phe Lys Thr Glu Ile Thr Leu Ala
                    1040                1045                1050
Asn Gly Glu Ile Arg Lys Arg Pro Leu Ile Glu Thr Asn Gly Glu
                    1055                1060                1065
Thr Gly Glu Ile Val Trp Asp Lys Gly Arg Asp Phe Ala Thr Val
                    1070                1075                1080
Arg Lys Val Leu Ser Met Pro Gln Val Asn Ile Val Lys Lys Thr
                    1085                1090                1095
Glu Val Gln Thr Gly Gly Phe Ser Lys Glu Ser Ile Leu Pro Lys
                    1100                1105                1110
Arg Asn Ser Asp Lys Leu Ile Ala Arg Lys Lys Asp Trp Asp Pro
                    1115                1120                1125
Lys Lys Tyr Gly Gly Phe Asp Ser Pro Thr Val Ala Tyr Ser Val
                    1130                1135                1140
Leu Val Val Ala Lys Val Glu Lys Gly Lys Ser Lys Lys Leu Lys
                    1145                1150                1155
Ser Val Lys Glu Leu Leu Gly Ile Thr Ile Met Glu Arg Ser Ser
                    1160                1165                1170
Phe Glu Lys Asn Pro Ile Asp Phe Leu Glu Ala Lys Gly Tyr Lys
                    1175                1180                1185
Glu Val Lys Lys Asp Leu Ile Ile Lys Leu Pro Lys Tyr Ser Leu
                    1190                1195                1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 1053
<212> TYPE: PRT
<213> ORGANISM: Staphylococcus aureus

<400> SEQUENCE: 2

Met Lys Arg Asn Tyr Ile Leu Gly Leu Asp Ile Gly Ile Thr Ser
1                5                  10                 15

Gly Tyr Gly Ile Ile Asp Tyr Glu Thr Arg Asp Val Ile Asp Ala Gly
                20                 25                 30

Val Arg Leu Phe Lys Glu Ala Asn Val Glu Asn Asn Glu Gly Arg Arg
                35                 40                 45

Ser Lys Arg Gly Ala Arg Arg Leu Lys Arg Arg Arg His Arg Ile
    50                  55                 60

Gln Arg Val Lys Lys Leu Leu Phe Asp Tyr Asn Leu Leu Thr Asp His
65                  70                 75                 80

Ser Glu Leu Ser Gly Ile Asn Pro Tyr Glu Ala Arg Val Lys Gly Leu
                85                 90                 95

Ser Gln Lys Leu Ser Glu Glu Glu Phe Ser Ala Ala Leu Leu His Leu
                100                105                110

Ala Lys Arg Arg Gly Val His Asn Val Asn Glu Val Glu Glu Asp Thr
                115                120                125

Gly Asn Glu Leu Ser Thr Lys Glu Gln Ile Ser Arg Asn Ser Lys Ala
    130                 135                140

Leu Glu Glu Lys Tyr Val Ala Glu Leu Gln Leu Glu Arg Leu Lys Lys
145                 150                155                160

Asp Gly Glu Val Arg Gly Ser Ile Asn Arg Phe Lys Thr Ser Asp Tyr
                165                170                175

Val Lys Glu Ala Lys Gln Leu Leu Lys Val Gln Lys Ala Tyr His Gln
                180                185                190

Leu Asp Gln Ser Phe Ile Asp Thr Tyr Ile Asp Leu Leu Glu Thr Arg
```

```
            195                 200                 205
Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                    245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
                275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                    325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
                355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                    405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                    485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                    565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
610                 615                 620
```

-continued

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
        660                 665                 670

Val Lys Ser Ile Asn Gly Gly Phe Thr Ser Phe Leu Arg Arg Lys Trp
    675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
        740                 745                 750

Ile Phe Ile Thr Pro His Gln Ile Lys His Ile Lys Asp Phe Lys Asp
    755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Leu Met Tyr His His
        820                 825                 830

Asp Pro Gln Thr Tyr Gln Lys Leu Lys Leu Ile Met Glu Gln Tyr Gly
    835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
        900                 905                 910

Arg Phe Asp Val Tyr Leu Asp Asn Gly Val Tyr Lys Phe Val Thr Val
    915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
        980                 985                 990

Glu Val Asn Met Ile Asp Ile Thr Tyr Arg Glu Tyr Leu Glu Asn Met
    995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

```
        Tyr Glu  Val Lys Ser Lys Lys  His Pro Gln Ile Ile  Lys Lys Gly
            1040             1045                1050
```

<210> SEQ ID NO 3
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 3
tgcgctggtt gatttcttct tgcgcttttt ggg         33

<210> SEQ ID NO 4
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 4
tgcgctggtt gatttcttct tgcgcttatt ggg         33

<210> SEQ ID NO 5
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 5
tgcgctggtt gatttcttct tgcgcatttt ggg         33

<210> SEQ ID NO 6
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 6
tgcgctggtt gatttcttct tgccctttt ggg         33

<210> SEQ ID NO 7
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 7
tgcgctggtt gattacttct tgcgcttttt ggg         33

<210> SEQ ID NO 8
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 8
tgcgctggtt gaattcttct tgcgcttttt ggg         33

<210> SEQ ID NO 9
<211> LENGTH: 33
<212> TYPE: DNA

```
<213> ORGANISM: Artificial Sequence
<220> FEATURE:
<223> OTHER INFORMATION: Completely synthesized in the lab.

<400> SEQUENCE: 9
tgcgctggtt cttttcttct tgcgcttttt ggg                              33

<210> SEQ ID NO 10
<211> LENGTH: 33
<212> TYPE: DNA
<213> ORGANISM: Artificial Sequence
<220> FEATURE:
<223> OTHER INFORMATION: Completely synthesized in the lab.

<400> SEQUENCE: 10
tgcgctggtt ctaatcttct tgcgcttttt ggg                              33
```

VARIANT CAS9 PROTEINS WITH IMPROVED DNA CLEAVAGE SELECTIVITY

CROSS REFERENCE TO RELATED APPLICATIONS

The present patent application claims priority to U.S. Provisional Patent Application Ser. Nos. 62/730,890, filed on Sep. 13, 2018, and 62/870,472, filed on Jul. 3, 2019, the entireties of which are hereby expressly incorporated herein by reference.

GOVERNMENT SUPPORT

This invention was made with government support under National Science Foundation Grant MCB-1716423 and National Institutes of Health Grant P20GM103640. The government has certain rights in the invention.

BACKGROUND

CRISPR-Cas (Clustered Regularly Interspaced Short Palindromic Repeats—CRISPR associated) systems are RNA-protein based adaptive immune systems present in bacteria and archaea. Using an RNA molecule as a guide, the CRISPR-Cas complexes cleave DNA and/or RNA of the invading genetic elements that carry a complementary region corresponding to the guide RNA. In the most current classification, CRISPR-Cas systems are organized into two classes and further into six types (I through VI) and several sub-types based on the locus organization and the Cas endonuclease that cleaves the intruding genetic element.

Cas9, the signature protein for the type II CRISPR systems, requires two native RNA components, CRISPR RNA (crRNA) and a trans-activating CRISPR RNA (tracrRNA), for its DNA targeting activity. The crRNA contains the "guide" region that is used for locating complementarity in the target DNA. These two RNA molecules can be fused to produce a single-guide-RNA (sgRNA) without affecting the functionality. The ease of using a single Cas9 protein and an sgRNA for DNA targeting has been monumental for genome editing and other applications such as site-specific DNA repression and activation, proteomic analyses, and is being investigated for use in gene therapy applications.

Cas9 is a multi-domain protein. Crystal structures of Cas9 orthologs from different subtypes of type II CRISPR reveal a common architecture, where the protein folds into a bi-lobed architecture consisting of a nuclease (NUC) lobe and a recognition (REC) lobe. The NUC and REC lobes are connected to each other by a long arginine-rich bridge helix (BH). The NUC lobe comprises two endonuclease domains, HNH and RuvC, and a domain responsible for recognizing the DNA protospacer-adjacent-motif (PAM), a 2-8 nucleotides (nt) long region that is essential to discriminate between self and foreign DNA. The REC lobe of Cas9 and BH are involved in subtype-specific tracrRNA-crRNA recognition.

The apo-Cas9 protein undergoes large conformational re-arrangement upon sgRNA binding to form the binary complex, including a 65 Å rigid body movement of the REC-III domain of REC lobe. The core region of the sgRNA makes extensive interactions with REC domains and the BH. A majority of the interactions of Cas9 with the crRNA-guide involves the RNA sugar-phosphate backbone, resulting in a solvent exposed pre-ordered "seed" region that is poised to search and locate a target DNA with an approximately 20 nt complementary segment called "protospacer".

The first step in DNA targeting by Cas9 is locating the PAM region in the target and the longevity of the ternary complex (Cas9-sgRNA-DNA) is enhanced by the presence of a cognate PAM flanking the protospacer. Following PAM recognition, the crRNA-guide region searches for complementarity in the flanking DNA by unwinding the DNA duplex subsequently forming an R-loop between the crRNA-guide and the protospacer. Once the complementarity between the target DNA and the RNA guide is established, the target DNA cleavage is brought about by two independent cleavage reactions performed by HNH on the strand complementary to the crRNA-guide and RuvC on the non-complementary DNA strand.

The binary complex undergoes a smaller degree of conformational change upon target DNA binding to form a ternary complex, mostly involving the HNH domain. Once the R-loop complementarity reaches 14-17 nt long, the HNH movement occurs, after which it is positioned ideally to cleave the complementary strand of DNA. The movement of HNH to the active position acts as an allosteric switch that activates the RuvC domain such that the coordinated activities of both endonuclease sites bring about a concerted DNA cleavage. The positioning of, not cleavage by, HNH is essential for RuvC activity when both endonuclease domains are present in the protein. It was shown that *Campylobacter jejuni* Cas9 nicks DNA using the RuvC domain when HNH domain is absent, indicating the complexities of the interplay between different domains of the protein. The coordinated activity also implements specificity in DNA cleavage. It was recently reported that REC-II domain has to move to facilitate the positioning of the HNH domain. Thus, the conformational changes in response to RNA and DNA binding not only enable ideal binding environments, but also impart fidelity in the cleavage process.

Even though relatively simple to use compared to other gene-editing techniques, Cas9's primary drawback is off-target DNA cleavage, which arises due to the tolerance of Cas9 to mismatches between the sgRNA-guide and the target DNA. The stringency of the interdependence between RNA-DNA complementarity and DNA cleavage efficiency varies along different regions of the protospacer. While PAM proximal mismatches greatly reduce DNA cleavage, PAM-distal mismatches are tolerated to varying degrees. Within the PAM proximal region, mismatches at different positions have been observed to differentially affect activity, with nt 3 to 6 having the most detrimental effects on target cleavage as compared to nt 1 and 2 and others beyond the $6^{th}$ nucleotide. In *Streptococcus pyogenes* (Spy) Cas9, the presence of PAM and at least 9 nt of perfect match in the seed region (PAM proximal region) is sufficient to produce a protein-RNA-DNA complex that has similar stability as that of a complex with fully matched (20 nt) target DNA, indicating that mismatches beyond the 9 nt seed region affect steps in the mechanism that are subsequent to stable ternary complex formation. The BH is an Arginine Rich Motif (ARM) and it is a universal feature of Cas9. BH functions to bridge the NUC and REC lobes and makes direct and indirect interactions with crRNA, tracrRNA and target DNA It has been shown in several Cas9 orthologs that mutating the arginine residues in the BH significantly reduces its activity.

at different $Mg^{2+}$ concentrations. Data shown were obtained with a reaction time of 15 minutes, and error bars represent standard error mean (SEM). Each experiment was typically conducted in replicates of three, using proteins from two different batches of purification.

Figure 4:
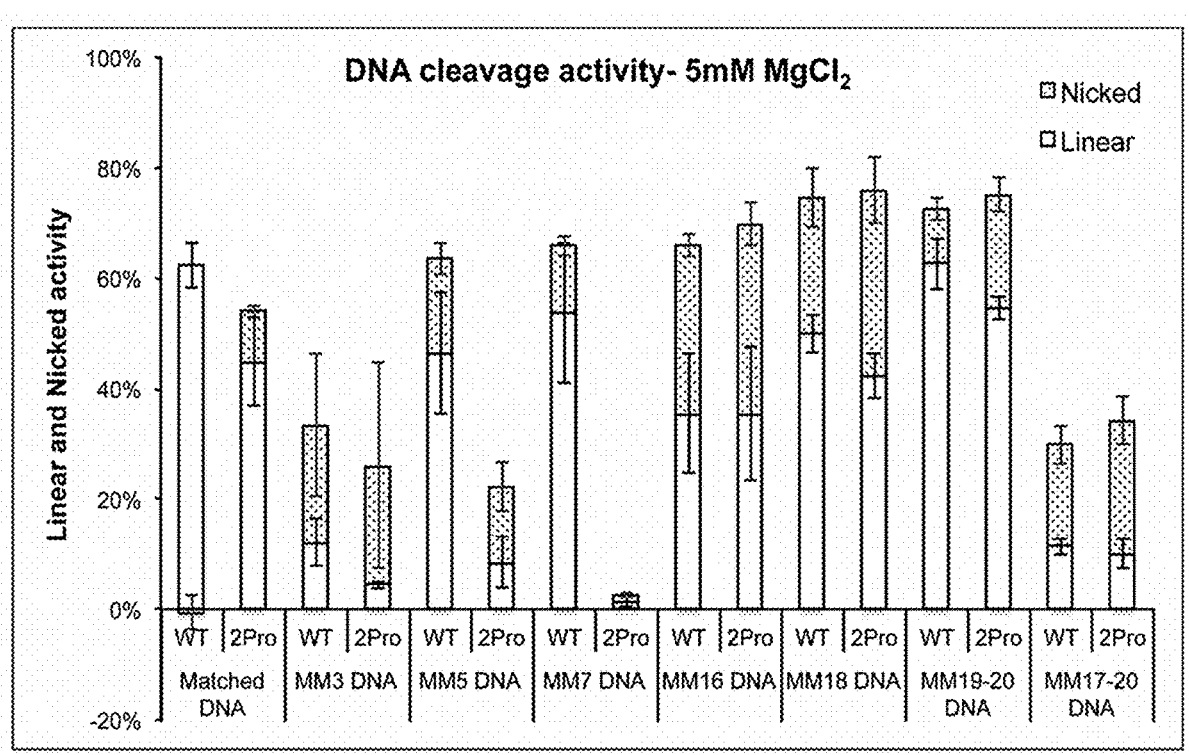

FIG. 4 compares SpyCas9$^{WT}$ and SpyCas9$^{2Pro}$ activities using sgRNA$^{del}$ on different DNA substrates at 5 mM $Mg^{2+}$ ions. Upper panel shows sequences (SEQ ID NOS: 3-10) of DNA substrates (the sequence of non-complementary DNA strand is shown) used in the present disclosure. Bold and underlined sequences are mismatches in the protospacer while annealing to sgRNA. Lower panel graph shows the total activity with separate regions indicating the percentage of nicked (stippled region) and linear products. The enzyme concentration was 50 nM. For matched DNA and MM5 DNA, there are nine and six replications respectively, while for the rest there are three replications. Error bars represent SEM.

Figure 5A:
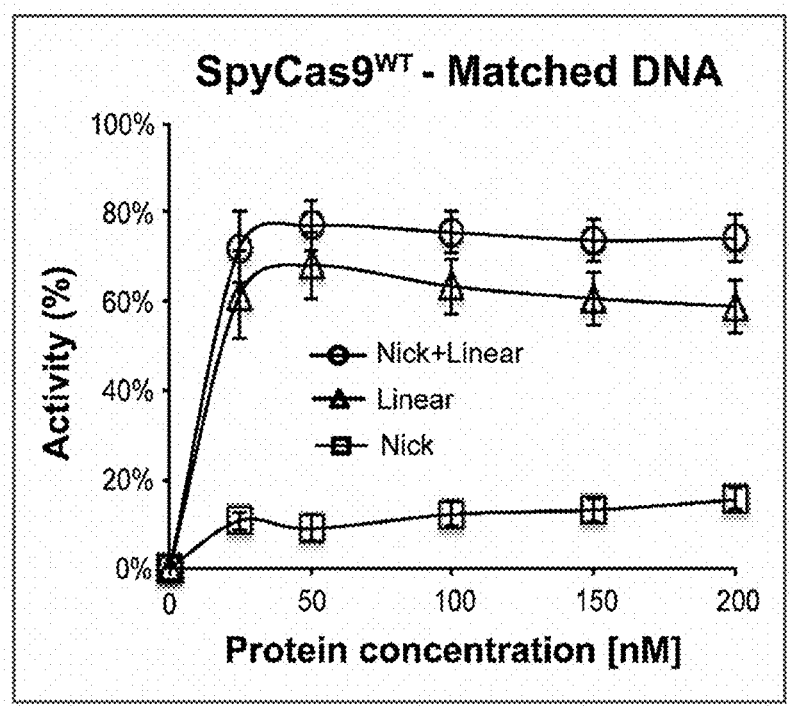
Figure 5A:
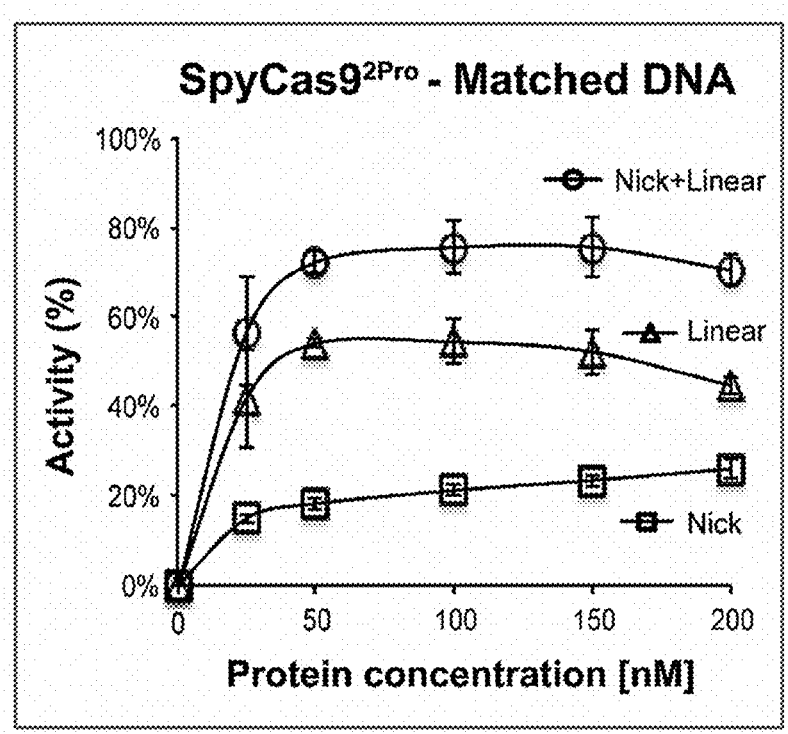

FIG. 5A shows a comparison of the cleavage pattern (linearization and nicking) of SpyCas9$^{WT}$ (upper panel) and SpyCas9$^{2Pro}$ (lower panel) with a fully matched DNA substrate at 5 mM $Mg^{2+}$ ions. The average values for nicked (%), linear (%), and nicked+linear (%) are plotted against protein concentration. Data were obtained from three replications with a reaction time of 15 minutes and error bars represent SEM.

Figure 5B:
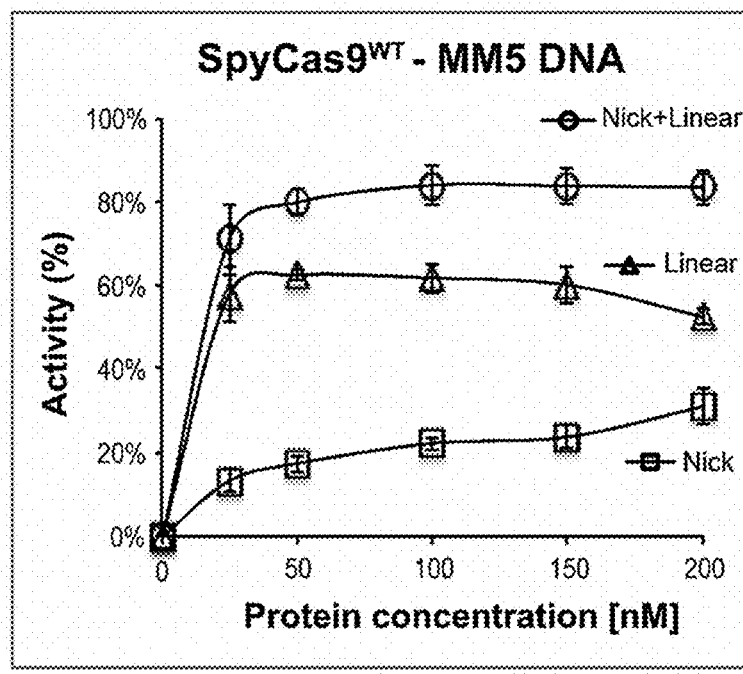
Figure 5B:
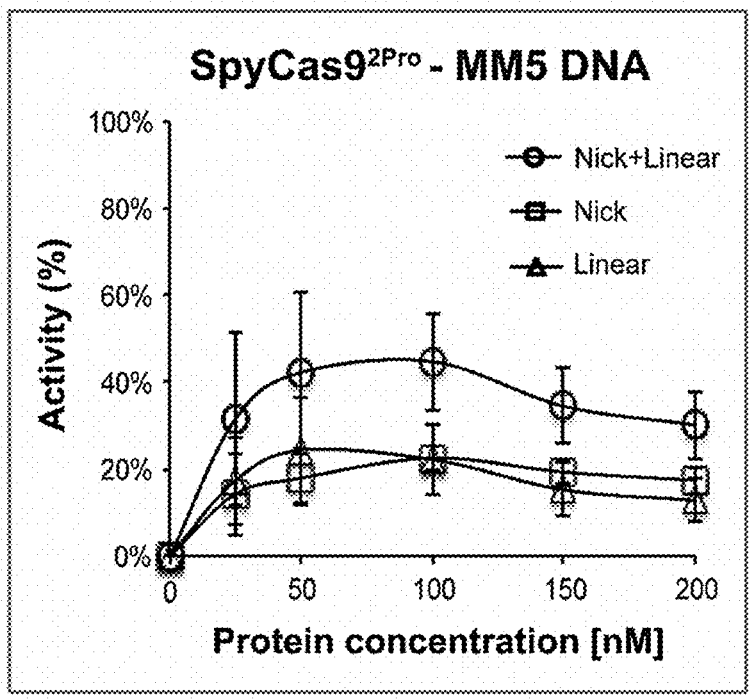

FIG. 5B shows a comparison of the cleavage pattern (linearization and nicking) of SpyCas9$^{WT}$ (upper panel) and SpyCas9$^{2Pro}$ (lower panel) with a mismatched DNA substrate at 5 mM $Mg^{2+}$ ions. The average values for nicked (%), linear (%), and nicked+linear (%) are plotted against protein concentration. Data were obtained from three replications with a reaction time of 15 minutes and error bars represent SEM.

Figure 6:
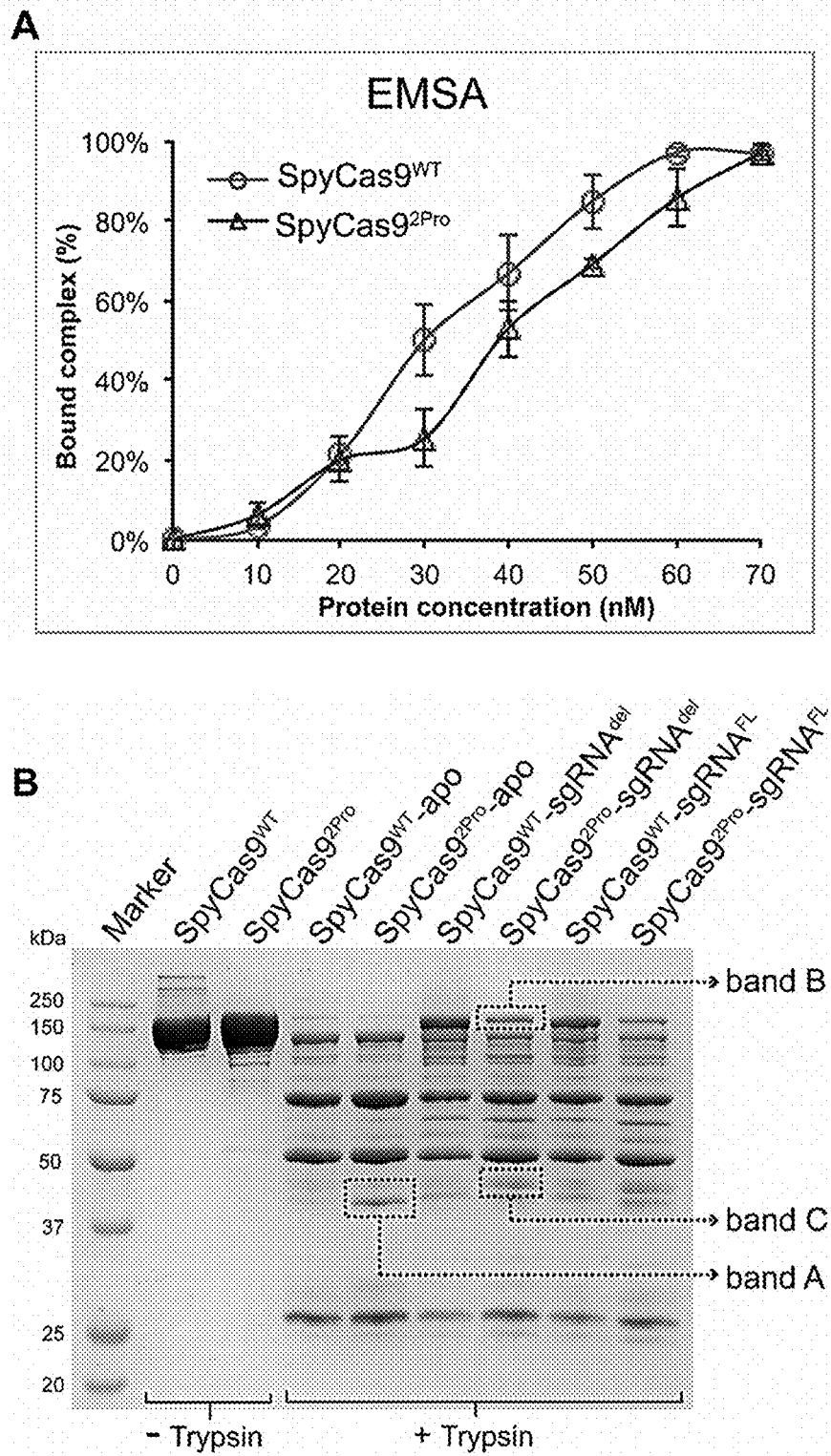

FIG. 6 shows RNA binding and limited proteolysis of SpyCas9$^{WT}$ and SpyCas9$^{2Pro}$. (A) shows quantification of binary complex formed by SpyCas9$^{2Pro}$ and SpyCas9$^{WT}$. EMSA was conducted using 5'-$^{32}$P labelled sgRNA$^{del}$. The protein concentration was increased from 10 nM to 70 nM relatively to sgRNA concentration (~50 nM). Graph shows the average of bound complex from three independent replications over different protein concentrations. The data indicate that the RNA binding property of SpyCas9$^{2Pro}$ is not significantly reduced compared to SpyCas9$^{WT}$. (B) shows results of trypsin digestion of SpyCas9$^{WT}$ and SpyCas9$^{2Pro}$ with or without sgRNA. In the apo-form, the digestion profiles for both proteins are similar except for increased intensity of band A in SpyCas9$^{2Pro}$. The sgRNA bound form of SpyCas9$^{2Pro}$ is not protected to the same extent as SpyCas9$^{WT}$-sgRNA complex (see the difference in intensity of band B). In addition, band C is more prominent in SpyCas9$^{2Pro}$-sgRNA complex, indicating conformational differences between the two binary complexes.

Figure 7A:
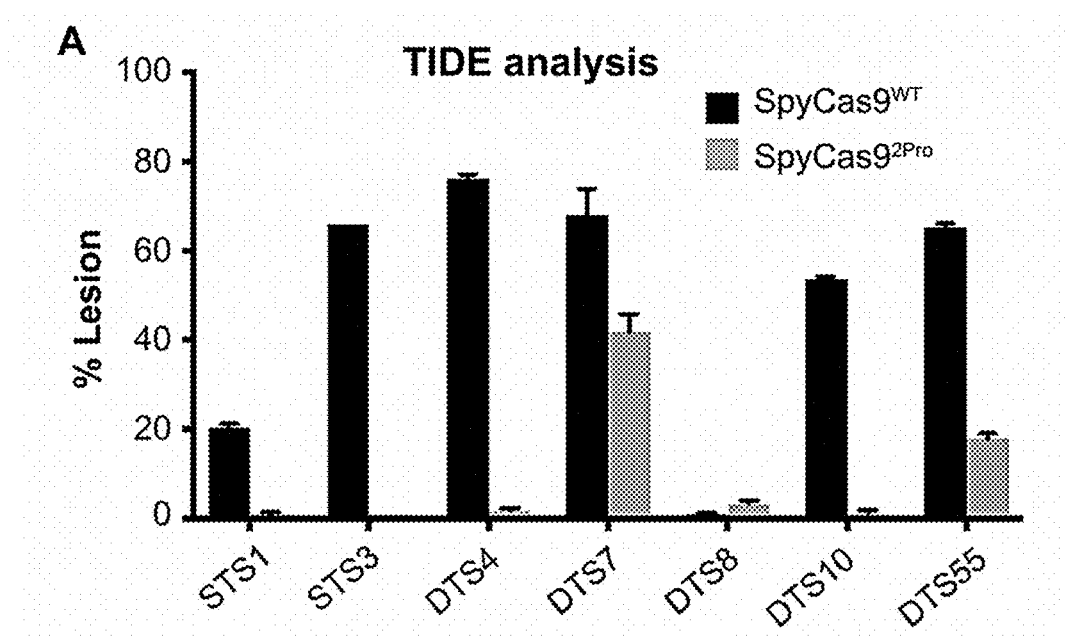

FIG. 7A is an activity analysis of SpyCas9$^{WT}$ and SpyCas9$^{2Pro}$ in HEK293T cells showing results of a TIDE analysis of cleavage by SpyCas9$^{WT}$ and SpyCas9$^{2Pro}$ at different genomic loci.

Figure 7B:
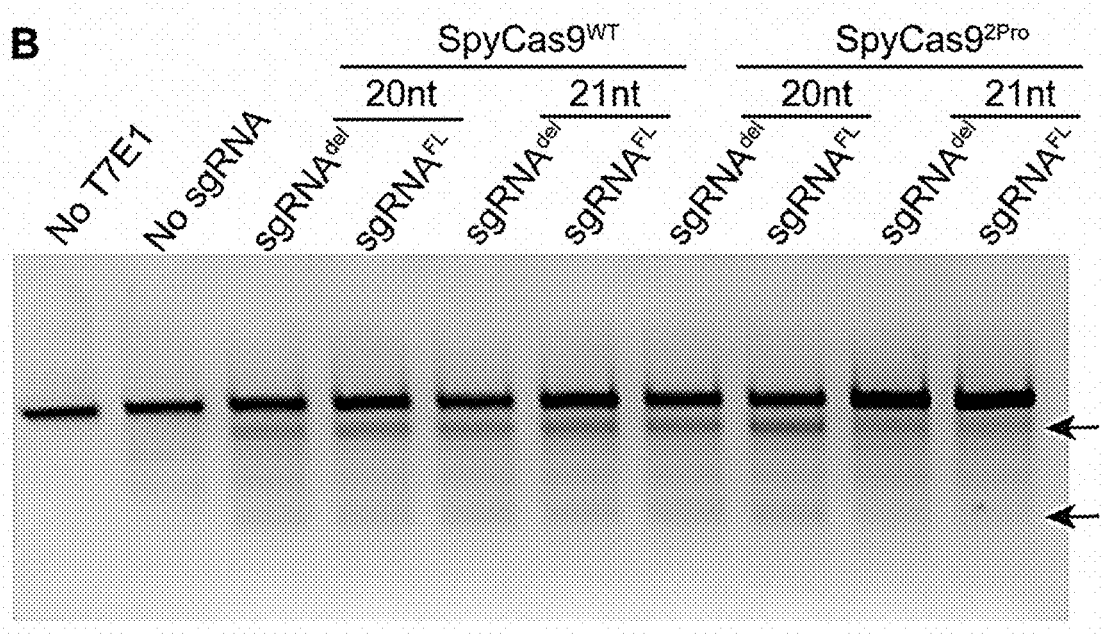

FIG. 7B is an activity analysis of SpyCas9$^{WT}$ and SpyCas9$^{2Pro}$ in HEK293T cells showing results of a T7 endonuclease assay for DTS7 spacer (with 20 nt or 21 nt of length) and using shortened (del) or full length (FL) repeat-tracrRNA region. Arrows indicate cleavage products produced by T7E1 on mismatches created as a result of Cas9 editing.

Figure 7C:
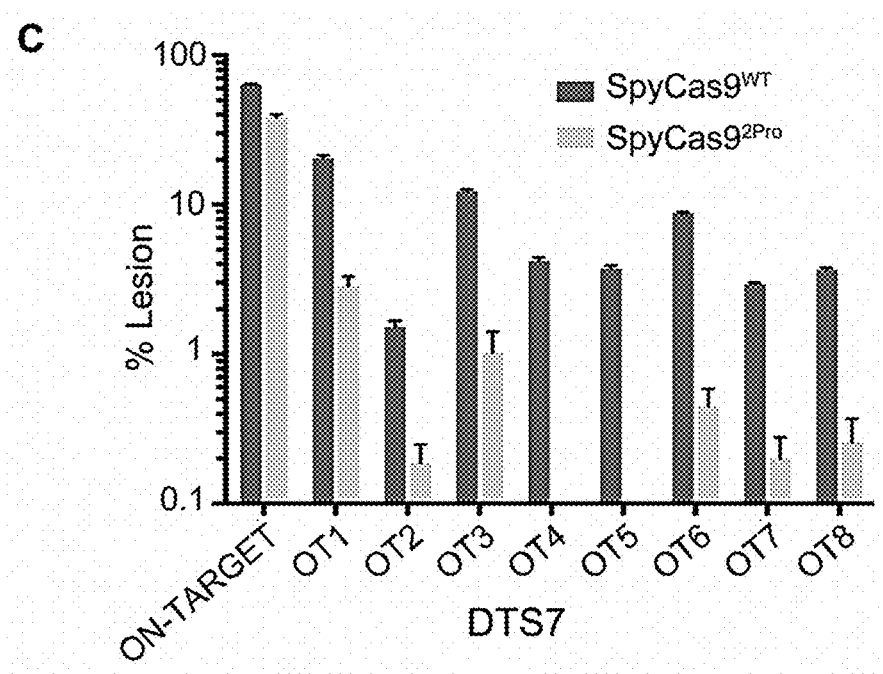

FIG. 7C shows off-target activity of SpyCas9$^{WT}$ and SpyCas9$^{2Pro}$ as measured by targeted deep sequencing, the unmodified controls show no editing.

DETAILED DESCRIPTION

The present disclosure is directed to variant Cas9 proteins comprising at least one amino acid substitution in the bridge helix (BH) portion of the protein, and which have improved DNA cleavage selectivity in comparison to the wild type version of the Cas9 protein. Certain embodiments comprise at least two amino acid substitutions in the BH portion. In particular embodiments, the at least one substitution is proline. In one embodiment, a mutant *Streptococcus pyogenes* Cas9 (SpyCas9) protein may comprise substitutions in either or both of positions L64 and K65. For example, one non-limiting embodiment is a mutant SpyCas9 protein (SpyCas9$^{2Pro}$) having proline substitutions at both of positions L64 and K65.

In certain embodiments, the present disclosure is also directed to BH variants of Cas9 orthologs of *Streptococcus pyogenes*, such as *Staphylococcus aureus* Cas9 (SauCas9—SEQ ID NO:2), including, but not limited to, substitutions of one or both of positions S49 and K50 thereof with proline, which have increased cleavage selectivity as compared to the wild type SauCas9 protein. Similar substitutions with proline may be made in homologous positions in the BH of other Cas9 orthologs, such as orthologs listed in FIGS. 2-3 of U.S. Provisional Application Ser. No. 62/870,472, filed on Jul. 3, 2019, which is expressly incorporated herein by reference. The present disclosure is also directed to nucleic acids encoding the variant proteins, vectors and host cells containing the nucleic acids, and methods of their use.

Before describing various embodiments of the present disclosure in more detail by way of exemplary description, examples, and results, it is to be understood that the present disclosure is not limited in application to the details of methods, constructs, cells, and compositions as set forth in the following description. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that other embodiments of the inventive concepts may be practiced without these specific details. In other instances, features which are well known to persons of ordinary skill in the art have not been described in detail to avoid unnecessary complication of the description.

All patents, published patent applications, and non-patent publications referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art.

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. Further, unless otherwise required by context, singular terms shall include pluralities and plural terms shall include the singular. Where used herein, the specific term "single" is limited to only "one". Use of the word "we" as a pronoun herein refers generally to laboratory personnel or other contributors who assisted in laboratory procedures and data collection and is not intended to represent an inventorship role by said laboratory personnel or other contributors in any subject matter disclosed herein.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the constructs, cells, compositions and methods used, or the variation that exists among the study objects. Further, in this detailed description and the appended claims, each numerical value (e.g., temperature or time) should be read once as modified by the term "about" (unless already expressly so modified), and then read again as not so modified unless otherwise indicated in context. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

Also, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1). Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 1-20, 10-50, 50-100, 100-1,000, 1,000-3,000, 2,000-4,000, etc.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

Protein variants disclosed herein may comprise conservative substitutions in portions of the BH region (e.g., amino acids 59-93 of SpyCas9 and amino acids 45-76 of SauCas9), as well as in other regions and domains of the protein. Substitutions may be selected from the natural amino acids. The natural amino acids include and may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V. Amino acids may be D or L enantiomers.

For purposes of classifying amino acids substitutions as conservative or nonconservative, amino acids are grouped in one embodiment as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same group. Non-conservative substitutions constitute exchanging a member of one of these groups for a member of another.

Tables of exemplary conservative amino acid substitutions have been constructed and are known in the art. In certain embodiments herein which reference possible substitutions, examples of interchangeable amino acids include, but are not limited to the following: arginine and lysine; glutamate and aspartate; serine and threonine; glutamine and asparagine; and valine, leucine and isoleucine. In other embodiments, the following substitutions can be made: Ala (A) by leu, ile, or val; Arg (R) by gln, asn, or lys; Asn (N) by his, asp, lys, arg, or gln; Asp (D) by asn, or glu; Cys (C) by ala, or ser; Gln (Q) by glu, or asn; Glu (E) by gln, or asp; Gly (G) by ala; His (H) by asn, gln, lys, or arg; Ile (I) by val, met, ala, phe, or leu; Leu (L) by val, met, ala, phe, or ile; Lys (K) by gln, asn, or arg; Met (M) by phe, ile, or leu; Phe (F) by leu, val, ile, ala, or tyr; Pro (P) by ala; Ser (S) by thr; Thr (T) by ser; Trp (W) by phe, or tyr; Tyr (Y) by trp, phe, thr, or ser; and Val (V) by ile, leu, met, phe, or ala.

Other considerations for amino acid substitutions include whether or not the residue is located in the interior of a protein or is solvent- (i.e., externally) exposed. For interior residues, conservative substitutions include for example: Asp and Asn; Ser and Thr; Ser and Ala; Thr and Ala; Ala and Gly; Ile and Val; Val and Leu; Leu and Ile; Leu and Met; Phe and Tyr; and Tyr and Trp. For solvent-exposed residues, conservative substitutions include for example: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; and Phe and Tyr.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an "A," a "G," a uracil "U" or a "C"). The term nucleobase also includes non-natural bases as described below. The term "nucleic acid" encompasses the terms "oligonucleotide" and "polynucleotide," each as a subgenus of the term "nucleic acid." In certain embodiments, the present disclosure is directed to nucleic acids (DNA and RNA) which encode the variant Cas9 proteins described.

As used herein, the terms "complementary" or "complement" also refer to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

The term "homologous" or "% identity" as used herein means a nucleic acid (or fragment thereof), or a protein (or a fragment thereof) having a degree of homology to the corresponding natural reference nucleic acid, or protein, that is at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% identical thereto. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl.

Acad. Sci. USA 1990, 87, 2264-2268, modified as in Karlin & Altschul, Proc. Natl. Acad. Sci. USA 1993, 90, 5873-5877.

Percentage sequence identities can be determined with protein sequences maximally aligned by the Kabat numbering convention. After alignment, if a particular polypeptide region is being compared with the same region of a reference polypeptide, the percentage sequence identity between the subject and reference polypeptide region is the number of positions occupied by the same amino acid in both the subject and reference polypeptide region divided by the total number of aligned positions of the two regions, with gaps not counted, multiplied by 100 to convert to percentage.

In one embodiment "% identity" represents the number of amino acids which are identical at corresponding positions in two sequences of a protein having the same or similar activity. For example, two amino acid sequences each having 100 residues will have at least 90% identity when 90 of the amino acids at corresponding positions are the same. Similarly, in one embodiment "% identity" represents the number of nucleotides which are identical at corresponding positions in two sequences of a nucleic acid encoding the same or similar polypeptides. For example, two nucleic acid sequences each having 100 nucleotides will have 90% identity when 90 of the nucleotides in homologous positions are the same.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Non-limiting applications include isolating a nucleic acid, such as a gene or a nucleic acid segment thereof, or detecting at least one specific mRNA transcript or a nucleic acid segment thereof, and the like. Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid, the length and nucleobase content of the target sequence, the charge composition of the nucleic acid, and to the presence or concentration of formamide, tetramethylammonium chloride or other solvent in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization to achieve varying degrees of selectivity of a nucleic acid towards a target sequence are used. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suit a particular application.

In certain embodiments herein, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or the like.

The term encoding" as used herein refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence" or "nucleic acid" encoding an amino acid sequence includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "bind," "binds," or "interacts with" means that one molecule recognizes and adheres to a particular second molecule in a sample or organism, but does not substantially recognize or adhere to other structurally unrelated molecules in the sample.

By the term "specifically binds," as used herein with respect to an antibody, is meant an antibody which recognizes a specific antigen, but does not substantially recognize or bind other molecules in a sample.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence of interest), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which includes an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, et al. Examples of viral vectors include, but are not limited to, adenoviral vectors, adeno-associated virus vectors, and retroviral vectors. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by attenuating the HIV virulence genes, for example, the genes env, vif, vpr, vpu, and nef are deleted making the vector biologically safe. In other embodiments of the present disclosure, a gamma retrovirus may be used as the transfecting agent.

Where used herein the term "wild-type" refers to the typical form (genotype and/or phenotype) of a bacterium, gene, nucleic acid, protein, or peptide as it occurs in nature and/or is the most common form in a natural population. In reference to a gene or nucleic acid, the term "mutation" refers to a gene or nucleic acid comprising an alteration in the wild type, such as but not limited to, a nucleotide deletion, insertion, and/or substitution. A mutation in a gene or nucleic acid generally results in either inactivation, decrease in expression or activity, increase in expression or activity, or another altered property of the gene or nucleic acid. In reference to a protein, the term "mutation" or "variant" refers to a protein comprising an alteration in the wild type, such as but not limited to, one or more amino acid deletions, insertions, and/or substitutions. A mutation in a protein may result in either inactivation, a decrease in activity or effect (e.g., binding), or an increase in activity or effect (e.g., binding or selectivity), or another altered property or effect of the protein.

EXAMPLES

Certain novel embodiments of the present disclosure, having now been generally described, will be more readily understood by reference to the following examples, which are included merely for purposes of illustration of certain aspects and embodiments of the present disclosure, and are not intended to be limiting. The following examples are to be construed, as noted above, only as illustrative, and not as limiting of the present disclosure in any way whatsoever. Those skilled in the art will promptly recognize appropriate variations from the various compositions, structures, components, procedures and methods.

Experimental

Methods

Protein Mutagenesis, Overexpression and Purification.

Proline substitutions were introduced at amino acid positions 64 and 65 of SpyCas9$^{WT}$ (SEQ ID NO:1) plasmid (Addgene-PMJ806, UniProt protein ID—CAS9 Q99ZW2) using polymerase chain reaction (PCR). The correctness of the sequence was confirmed by DNA sequencing covering the whole reading frame of the gene. Sequence-confirmed clones were transformed into *Escherichia coli* Rosetta strain 2 (DE3) for protein expression. Protein purification followed published protocols.

RNA Transcription.

The present work used two sgRNAs, a full-length (122 nt, sgRNA$^{FL}$) and a variant with deletions in the repeat-antirepeat region (98 nt, sgRNA$^{del}$). The guide region of both the sgRNAs was 20 nt long. The sequences were ordered as gBlock gene fragments from Integrated DNA Technologies (IDT), and cloned into pUC19 vector in between KpnI and EcoRI sites and transformed into DH5a cells [New England Biolabs (catalog number C2987H), for sgRNA$^{FL}$) and E. cloni cells [Lucigen (catalog number 60106-1), for sgRNA$^{del}$]. E. cloni cells facilitated production of sgRNA$^{del}$ without mutations in the gene sequence. To facilitate in vitro transcription, a T7 promoter sequence was introduced ahead of the sgRNA sequence, and a BbsI restriction site was placed to linearize the plasmid at the end of the sgRNA sequence. The BbsI-linearized plasmids were used as template for in vitro transcription. The transcription reaction followed established protocols.

In-Vitro DNA Cleavage Assays.

Protospacer strands for the MM5 DNA (mismatched substrate) were ordered as oligos from IDT, annealed and ligated into pUC19 vector. The oligos contained a 30 nt long protospacer with a 20 nt match to the guide region towards the 3' end and a GGG protospacer adjacent motif (PAM). The oligo was inserted between BamHI and EcoRI sites of pUC19. Wild-type substrate and other mismatched (MM) substrates (MM3, MM7, MM16, MM18, MM19-20, MM17-20) were generated with mutagenic primers using MM5 plasmid following either site-directed mutagenesis, Sequence and Ligation Independent Cloning (SLIC), or Single-Primer Reactions IN Parallel (SPRINP) method and transformed into DH5c or E. cloni cells.

For cleavage assay, protein was diluted to 1 µM in 20 mM HEPES pH 7.5, 150 mM KCl, 2 mM TCEP, and 2 mM EDTA. The sgRNA was annealed using the following steps: heat at 95° C. for 2 minutes, cool at room temperature for 2 minutes, add annealing buffer (20 mM TRIS-HCl pH 7.5, 100 mM KCl, 1 mM MgCl$_2$), and transfer it back to the heat block that has been turned off for slow cooling. The cleavage assays were carried out in a final volume of 10 µL and typically contained the following: 20 mM HEPES pH 7.5, 150 mM KCl, 2 mM TCEP, 100 ng plasmid (substrate DNA). MgCl$_2$ was at 1 mM, 5 mM, or 10 mM concentration. The protein-RNA was at equimolar ratio and the concentration varied for the different experiments. There was no pre-incubation of protein and RNA; protein was added as the last component of the cleavage reaction. The reaction was carried out at 37° C. for 15 minutes. The reaction was stopped using 50 mM EDTA and 1% SDS and products were resolved on a 1% agarose gel. The gel was post-stained with ethidium bromide and imaged using a BioRad ChemiDoc MP apparatus.

To quantify the cleavage activities, each gel image was analyzed using the Image J software to record intensities corresponding to nicked (N), linear (L), and supercoiled (SC) bands, which are designated respectively as $I_N$, $I_L$ and $I_{SC}$. Background-corrected total activity (TA) was calculated as following:

$$TA(\%) = \left[\frac{I_N + I_L}{I_N + I_L + I_{SC}} - \left(\frac{I_N + I_L}{I_N + I_L + I_{SC}}\right)_0\right] \times 100 \quad (1)$$

with the values with the "0" subscript $$\left[e.g., \left(\frac{I_N + I_L}{I_N + I_L + I_{SC}}\right)_0\right]$$

representing those calculated with the respective signals observed at the no enzyme control lane of each gel.

To compare the total activities, $$TA_{\left(\frac{2Pro}{WT}\right)},$$

the ratio of the total activity between SpyCas9$^{2Pro}$ and SpyCas9$^{WT}$, was computed following equations 1a through 1c.

First, at each enzyme complex concentration, the value $$ta_{\left(\frac{2Pro}{WT}\right)}$$

was computed as:

$$ta_{\left(\frac{2Pro}{WT}\right)} = \frac{TA(SpyCas9^{2Pro})}{TA(SpyCas9^{WT})} \quad (1a)$$

Since all measurements showed saturation behaviors at enzyme complex concentrations above 50 nM (see Results), $$ta_{\left(\frac{2Pro}{WT}\right)}$$

values at 100 nM, 150 nM, and 200 nM protein-RNA complex concentration were averaged:

$$<ta_{(\frac{2Pro}{WT})}> = \left\{\left[ta_{(\frac{2Pro}{WT})}\right]_{100} + \left[ta_{(\frac{2Pro}{WT})}\right]_{150} + \left[ta_{(\frac{2Pro}{WT})}\right]_{200}\right\}/3 \quad (1b)$$

To account for experimental errors, $$<ta_{(\frac{2Pro}{WT})}>$$

values from different replications were averaged, and designated as $$TA_{(\frac{2Pro}{WT})},$$

which was used to evaluate differences between SpyCas9$^{2Pro}$ and SpyCas9$^{WT}$:

$$TA_{(\frac{2Pro}{WT})} = \frac{1}{n}\sum_{i=1}^{n} <ta_{(\frac{2Pro}{WT})}>_i \quad (1c)$$

with n representing the number of replications (n≥3).

To analyze the effect of BH-loop mutation on the type of products produced, background corrected nicked and linear products were calculated as:

$$\text{Nicked (\%)} = \left[\frac{I_N}{I_N + I_L + I_{SC}} - \left(\frac{I_N}{I_N + I_L + I_{SC}}\right)_0\right] \times 100 \quad (2)$$

$$\text{Linear (\%)} = \left[\frac{I_L}{I_N + I_L + I_{SC}} - \left(\frac{I_L}{I_N + I_L + I_{SC}}\right)_0\right] \times 100 \quad (3)$$

with the values with the "0" subscript representing those calculated with the respective signals observed at the no enzyme control lane of each gel. In addition, $R_{L/N}$, the ratio of Linear vs. Nicked DNAs, was calculated from the background-corrected Linear and Nicked products as following:

$$R_{L/N} = \frac{\text{Linear}}{\text{Nicked}} = \frac{\left(\frac{I_L}{I_N + I_L + I_{SC}}\right) - \left(\frac{I_L}{I_N + I_L + I_{SC}}\right)_0}{\left(\frac{I_N}{I_N + I_L + I_{SC}}\right) - \left(\frac{I_N}{I_N + I_L + I_{SC}}\right)_0} \quad (4)$$

For each reported data point, average values were obtained from a minimum of three replications. Standard deviation (SD) and standard error of mean (SEM) were calculated based on the number of replications using the following equations:

$$SD = \sqrt{\Sigma((R - R_{AV})^2 \div (n-1))} \quad (5)$$

where R is a data value from each replication, $R_{AV}$ is average of data values of all the replications, and n is the number replications.

$$SEM = SD \div \sqrt{n} \quad (6)$$

where n is the number replications.

Electrophoretic Mobility Shift Assay (EMSA).

sgRNA$^{del}$ was dephosphorylated using Alkaline phosphatase (New England Biolabs) and 5' end labelled with $^{32}$P (γ-$^{32}$P ATP purchased from PerkinElmer) using T4 polynucleotide kinase (New England Biolabs). The labeled sgRNA$^{del}$ was purified using BioSpin column P-30 (BioRad) and a 100% recovery was assumed for calculations. The binding reaction was setup with increasing concentrations of protein (10 nM to 70 nM) at a constant RNA concentration of ~50 nM in a buffer containing 20 mM HEPES pH 7.5, 150 mM KCl, 2 mM TCEP, 1 mM MgCl$_2$. The exact amount of sgRNA may be lower since the concentration was not measured after the labeling procedure. After incubation at room temperature for 15 minutes, the components were resolved on a 6% native acrylamide gel. The gel and the running buffer composition included 0.25× Tris-Borate (TB) buffer pH 8.6 and 1 mM MgCl$_2$. The bands were visualized by phosphor imaging with Typhoon FLA 7000 system (GE life sciences). Three independent replications of the assay were performed. Graph was generated by plotting the average of three replications of bound complex over different protein concentrations and SEM is shown.

Limited Proteolysis.

SpyCas9 (6 μg) with or without bound sgRNA was digested with 0.0125 μg of trypsin (480:1 mass ratio) in a buffer containing 50 mM Tris-HCl pH 8.0 and 20 mM CaCl$_2$. For the sgRNA-bound reactions, there was a pre-incubation of protein and sgRNA$^{del}$ or sgRNA$^{FL}$ (protein to RNA ratio, 1:1.2) for 10 minutes at room temperature before the addition of trypsin. The digestion was stopped at 15 minutes with SDS-PAGE dye and the samples were resolved on a 10% SDS-PAGE gel. The protein bands were visualized by coomassie brilliant blue G-250 staining.

Cell-Based Activity Assay.

The SpyCas9$^{2Pro}$ construct used for genome editing study was made from wild-type gene backbone, pCSDest2-SpyCas9-NLS-3XHA-NLS (Addgene #69220), following the same method that was used to generate the bacterial SpyCas9$^{2Pro}$ variants. The sgRNA$^{del}$ backbone (pLKO.1-puro-U6) was obtained from Addgene (50920) and the guide region was replaced for the different target sites that were tested. Full-length sgRNA for the cell-based study was constructed by Gibson assembly method using the pLKO.1-puro-U6 backbone.

We used separate pCSDest2-SpyCas9-NLS-3XHA-NLS (driven by the CMV IE94 promoter) and pLKO.1-puro-U6sgRNA (driven by the U6 promoter) plasmids for the expression of SpyCas9 and its sgRNA. Cell-based assays followed previously-published protocols. The culturing medium for HEK293T cells contained DMEM with 10% FBS and 1% Penicillin/Streptomycin (Gibco) and the cells were grown in a 37° C. incubator supplemented with 5% CO$_2$. 200 ng Cas9-expressing plasmid, 200 ng sgRNA-expressing plasmid and 10 ng mCherry plasmid were transfected into ~1.5×10$^5$ cells using Polyfect transfection reagent (Qiagen) in a 24-well plate, following manufacturer's protocol. The mCherry plasmid was used to analyze the quality of transfection. The genomic DNA was extracted using DNeasy Blood and Tissue kit (Qiagen) after 72 hours of transfection. PCR-amplification was carried out using 50 ng of genomic DNA and primers specific for each genomic site with High Fidelity 2×PCR Master Mix (New England Biolabs). Indel analysis was performed by TIDE (Tracking of Indels by Decomposition) using 20 ng of purified PCR product (Zymo Research). The trace files were analyzed using the TIDE web tool. For T7E1 analysis, 0.5 μl T7 Endonuclease I (10 U/μl, New England Biolabs) was added to 10 μl of pre-annealed PCR product in 1×NEB Buffer 2 for 1 hour. The bands were resolved on a 2.5% agarose gel and visualized using SYBR-safe stain (ThermoFisher Scientific).

Off-Target Analysis by Targeted DNA Deep-Sequencing.

For off-target DNA cleavage analysis, we used sites that were identified as off-targets for DTS7 editing through GUIDE-seq analysis. The genomic DNA following transfection was used for deep-sequencing. We used a two-step PCR amplification to produce DNA fragments for on-target and off-target sites following previous protocols. The first step used locus-specific primers containing universal overhangs with complementary ends to the TruSeq adaptor sequences, while the second step used a universal forward primer and an indexed reverse primer to introduce the TruSeq adaptors. The PCR program is as per published protocols. Equal amounts of the products from each treatment group were mixed and purified using DNA Clean & Concentrator kit (Zymo Research). The library was deep sequenced using a paired-end 150 bp MiSeq run. The sequencing results and statistical analysis were done using R as described before.

Results

Proline Substitutions in the BH-Loop Affect Total Activity on DNA Targets.

Figure 1A:
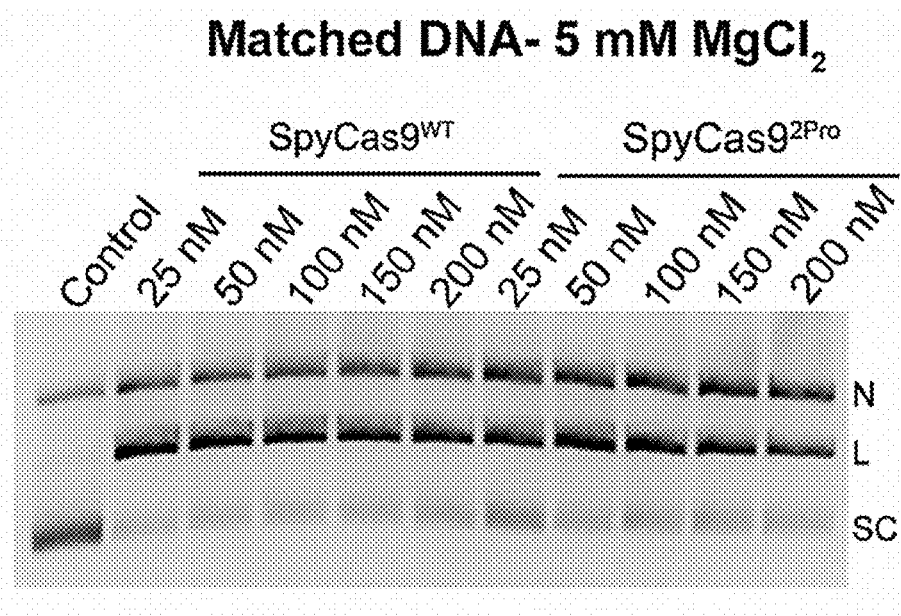
FIG. 1A compares total SpyCas9$^{WT}$ (SEQ ID NO:1) and SpyCas9$^{2Pro}$ activities with a fully matched DNA substrate at 5 mM $Mg^{2+}$. Shown is a representative gel presenting the DNA cleavage with varying amounts of protein:sgRNA complex. Supercoiled (SC), linear (L), and nicked (N) DNA bands are indicated. Data were obtained with a reaction time of 15 minutes, and error bars represent standard error mean (SEM). Each experiment was typically conducted in replicates of three, using proteins from two different batches of purification.
Figure 1B:
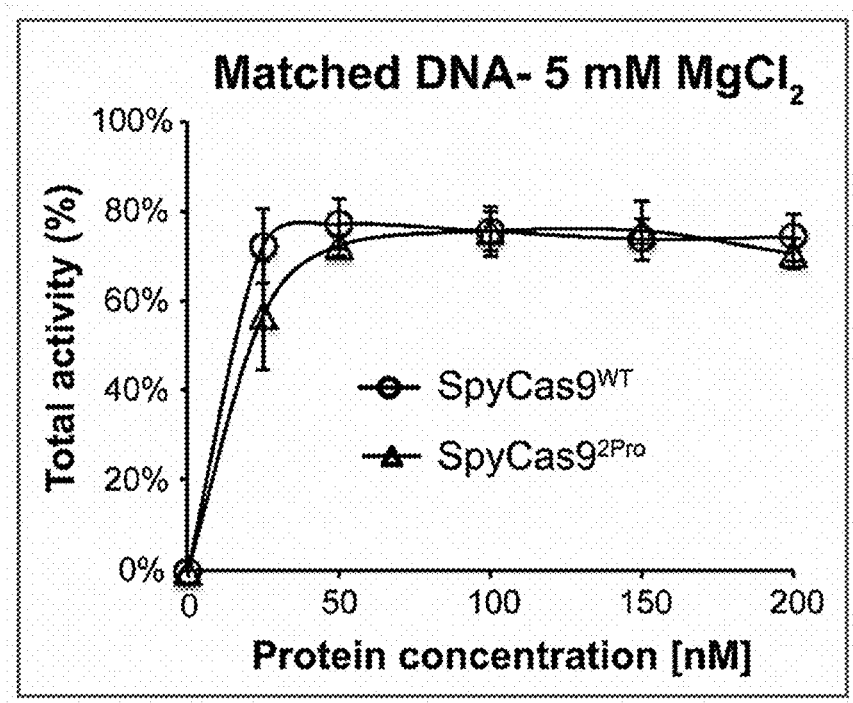
FIG. 1B shows the results of FIG. 1A plotted as total activity vs. the enzyme complex concentration. Average values from three replications were plotted against protein concentrations.

To investigate the role of the BH-loop in Cas9 activity, we substituted two amino acids in this loop of SpyCas9 (L64 and K65) with prolines (SpyCas9$^{2Pro}$). DNA cleavage activity assays were performed at different Mg$^{2+}$ concentrations using varying concentrations of an enzyme complex containing equimolar Cas9 and sgRNA. FIGS. 1A-3 show data obtained with an sgRNA having deletions in the repeat and tracrRNA regions (designated herein as sgRNA$^{del}$). At a total reaction time of 15 minutes, for each concentration of the enzyme-RNA complex tested, SpyCas9$^{WT}$ and SpyCas9$^{2Pro}$ gave similar total activity (sum of linear and nicked products, equation 1) with a DNA substrate containing a 20 nt target sequence complementary to the guide region of the sgRNA$^{del}$ (matched DNA) at 5 mM Mg$^{2+}$ (FIGS. 1A-B). Very similar data were obtained at 10 mM Mg$^{2+}$ (data not shown). The total activity of both SpyCas9$^{2Pro}$ (43%) and SpyCas9$^{WT}$ (59%) was diminished at 1 mM Mg$^{2+}$ compared to that at 5 mM and 10 mM Mg$^{2+}$, and the reduction was more pronounced for SpyCas9$^{2Pro}$ (data not shown). In addition, experiments with a full-length sgRNA (sgRNA$^{FL}$) that contains the full repeat-antirepeat regions showed similar activity for both SpyCas9$^{2Pro}$ and SpyCas9$^{WT}$ at 10 mM (~80% for both) and a lower activity at 1 mM Mg$^{2+}$ (~54% and ~67% respectively) (data not shown). This indicates that the extra regions present in sgRNA$^{FL}$ slightly enhance the cleavage activity under low Mg$^{2+}$ concentrations, but do not provide significant favorable interactions that may impact functional studies of the BH-loop substitutions.

Figure 2A:
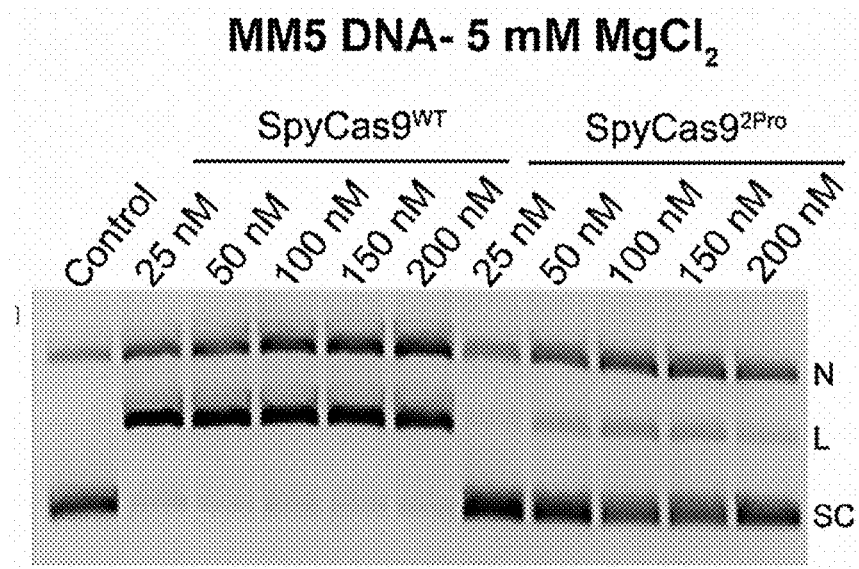
FIG. 2A compares total SpyCas9$^{WT}$ and SpyCas9$^{2Pro}$ activities with a mismatched DNA (MM5) substrate at 5 mM $Mg^{2+}$. Organization of the panel is the same as that in FIG. 1A. Data were obtained with a reaction time of 15 minutes, and error bars represent standard error mean (SEM). Each experiment was typically conducted in replicates of three, using proteins from two different batches of purification.
Figure 2B:
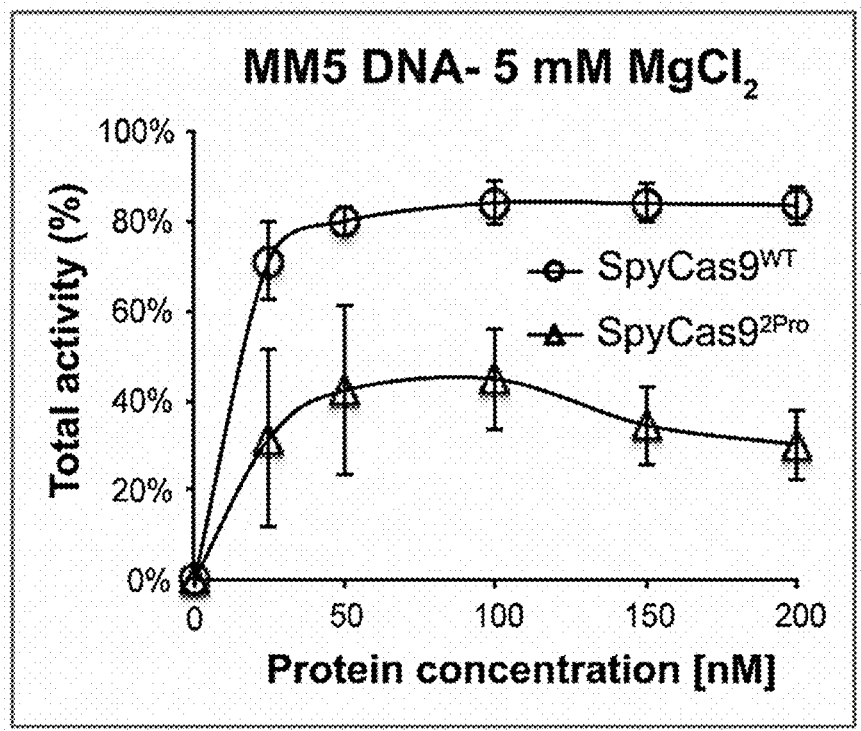
FIG. 2B shows the results of FIG. 2A plotted as total activity vs. the enzyme complex concentration. Average values from three replications were plotted against protein concentrations.

We further tested the effect of BH-loop mutation on DNA targets containing mismatches (MM) to the sgRNA guide (SEQ ID NOS:3-10 in FIG. 4). At 15-minutes reaction time, with a substrate containing a mismatch at the 5$^{th}$ nt from the PAM proximal side (MM5) and at 1 mM Mg$^{2+}$ concentration, SpyCas9$^{2Pro}$ exhibited very minimal total activity (~5%), while SpyCas9$^{WT}$ showed ~50% DNA cleavage (data not shown). At 5 mM Mg$^{2+}$, SpyCas9$^{2Pro}$ regained ~40% total cleavage with MM5, while total activity of SpyCas9$^{WT}$ increased to ~80% (FIGS. 2A-2B). The total activity at 10 mM Mg$^{2+}$ increased to ~60% for SpyCas9$^{2Pro}$ and to ~85% for SpyCas9$^{WT}$ (data not shown), indicating that higher Mg$^{2+}$ concentration can only partially compensate the effect caused by the BH-loop mutation.

Figure 3:
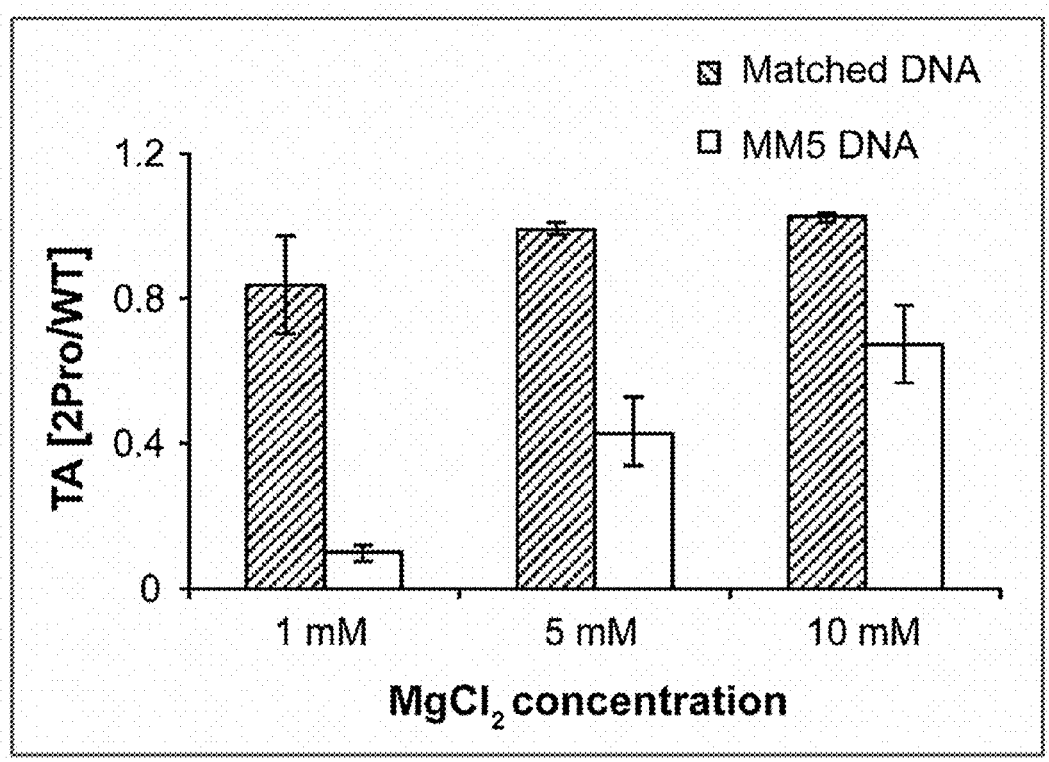
FIG. 3 compares the averaged ratio of total DNA cleavage activities between SpyCas9$^{2Pro}$ and SpyCas9$^{WT}$, $$TA_{\left(\frac{2Pro}{WT}\right)},$$

Repetitions for each of the DNA cleavage experiments gave characteristically very similar behaviors on the dependence of enzyme concentrations, although the absolute values of the activities show some variations, presumably reflecting variability in the amount of active enzyme complex in the different preparations. In addition, all measurements showed saturation behaviors at enzyme complex concentrations above 50 nM (FIGS. 1A-2B). Therefore, to quantitatively evaluate differences between SpyCas9$^{2Pro}$ and SpyCas9$^{WT}$, the ratio of the total activity between SpyCas9$^{2Pro}$ and SpyCas9$^{WT}$, $$TA_{\left(\frac{2Pro}{WT}\right)}$$

was calculated at saturating enzyme concentrations from multiple repetitions (see equations 1a-1c). The analyses show that with the matched DNA substrate, $$TA_{\left(\frac{2Pro}{WT}\right)}$$

is close to 1 at all three Mg$^{2+}$ concentrations tested (FIG. 3). For the mismatched substrate MM5, $$TA_{\left(\frac{2Pro}{WT}\right)}$$

values are all significantly less than 1, increasing from 0.1 at 1 mM Mg$^{2+}$ to 0.7 at 10 mM Mg$^{2+}$ (FIG. 3). Together with the results from varying protein-RNA concentrations (FIGS. 2A-B), the results indicate that total activity of SpyCas9$^{2Pro}$ is compromised against the MM5 substrate, although the activity can be partially restored at higher Mg$^{2+}$ concentrations.

Effects of BH-Loop Proline Substitution on Total Activity Vary Depending on the Mismatch Positions.

Expanding on the finding that total activity of SpyCas9$^{2Pro}$ is compromised against the MM5 mismatched substrate, we investigated how the positioning of the mismatch affects SpyCas9$^{2Pro}$ activity. Studies on the matched and MM5 substrates have shown that the activity levels plateau at a protein-RNA concentration of 50 nM and above, and that the activity levels vary depending on Mg$^{2+}$ concentrations (FIGS. 1A-2B). Based on these results, an enzyme complex concentration of 50 nM and Mg$^{2+}$ concentrations of 1 mM and 5 mM were used to conduct detailed analysis of the effect of mismatch positions on DNA cleavage with the BH-loop substitution.

It was recently established that positions 3-6 at the PAM proximal side are more important than positions 1-2 for target DNA cleavage by SpyCas9. We tested the effect of mismatches at the 3$^{rd}$ and 7$^{th}$ nt positions (MM3 and MM7, FIG. 4, upper panel) on target DNA cleavage and compared it with that of MM5. Even though the total activity of both SpyCas9$^{2Pro}$ and SpyCas9$^{WT}$ were reduced on MM3 (26% and 33% respectively) and MM5 (13% and 50% respectively), SpyCas9$^{2Pro}$ has a greater reduction compared to SpyCas9$^{WT}$ (FIG. 4, lower panel). The most significant difference was found for the MM7 substrate, where SpyCas9$^{WT}$ showed a cleavage of 66% while SpyCas9$^{2Pro}$ possessed only 3% activity at 5 mM Mg$^{2+}$ (FIG. 4, lower panel). Similar results were observed at 1 mM Mg$^{2+}$ concentration, where SpyCas9$^{WT}$ possessed 43% cleavage and SpyCas9$^{2Pro}$ showed no significant activity (5%) on MM7 (data not shown). These results show that SpyCas9$^{2Pro}$ is more effective in discriminating PAM-proximal mismatches than SpyCas9$^{WT}$ and the level of enhanced discrimination depends on the mismatch position.

We then tested whether the BH-loop mutation will affect the cleavage of DNA substrates with mismatches at the PAM-distal side (FIG. 4). Both single and multiple mutations were created at the PAM distal segment of the substrate (MM16, MM18, MM19-20 and MM17-20, FIG. 4, upper panel). The cleavage activity on substrates with single mutations at 16$^{th}$(SpyCas9$^{WT}$ at 66% vs. SpyCas9$^{2Pro}$ at 70%) and 18$^{th}$ (SpyCas9$^{WT}$ at 74% vs. SpyCas9$^{2Pro}$ at 76%) nt positions at 5 mM Mg$^{2+}$ were slightly higher for SpyCas9$^{2Pro}$ compared to SpyCas9$^{WT}$ (FIG. 4, lower panel). An analysis of the same reaction at 1 mM Mg$^{2+}$ shows 18% for SpyCas9$^{WT}$ and 33% for SpyCas9$^{2Pro}$ for MM16 and 44% for SpyCas9$^{WT}$ and 28% for SpyCas9$^{2Pro}$ for MM18 (data not shown). A double mutant at 19$^{th}$ and 20$^{th}$ nt positions (MM19-20) has similar activities with both SpyCas9$^{WT}$ and SpyCas9$^{2Pro}$ (~70% at 5 mM for both proteins, and ~32% for SpyCas9$^{WT}$ and ~24% for SpyCas9$^{2Pro}$ at 1 mM Mg$^{2+}$, FIG. 4, lower panel). A quadruple mutant from positions 17$^{th}$ to 20$^{th}$ (MM17-20) has negligible cleavage at 1 mM Mg$^{2+}$ and the cleavage increased to ~30% for SpyCas9$^{WT}$ and ~34% SpyCas9$^{2Pro}$ in the presence of 5 mM Mg$^{2+}$ (FIG. 4, lower panel). Overall, the data indicate that the difference in activity between SpyCas9$^{2Pro}$ and SpyCas9$^{WT}$ are much smaller on the PAM-distal mismatched substrates as compared to the PAM-proximal ones.

To further characterize the activity of SpyCas9$^{2Pro}$, the reaction rates for precursor cleavage ($k_{obs}$) were measured for the matched, MM5, and MM18 DNA targets [SI methods, SM 3]. At 50 nM protein-RNA concentration, SpyCas9$^{2Pro}$ cleaves the MM5 DNA 5.8 times slower compared to SpyCas9$^{WT}$, while a reduction of 2.2 times was observed for the matched DNA. This is consistent with the reduced total activity observed (FIGS. 1A-2B) and supports the conclusion that SpyCas9$^{2Pro}$ is compromised against the PAM-proximal mismatched MM5 substrate. Since SpyCas9$^{2Pro}$ can eventually attain a similar total activity on matched DNA (FIGS. 1A-2B), these data suggest that there are differences in the DNA cleavage mechanisms of SpyCas9$^{WT}$ and SpyCas9$^{2Pro}$. Interestingly, SpyCas9$^{2Pro}$ cleaves MM18, a PAM-distal mismatch, at a slightly higher rate (1.9 times) compared to SpyCas9$^{WT}$. This is consistent with the slightly higher total activities observed for PAM-distal mismatches (FIG. 4) and suggest that the BH-loop variations induce differences in target DNA engagement with respect to PAM-proximal and PAM-distal mismatches. Further studies are required to completely characterize these differences.

Proline Substitution in the BH-Loop Reduces Linearization of Mismatched Substrates.

During analyses of DNA cleavage by SpyCas9$^{2Pro}$ and SpyCas9$^{WT}$, we observed that the two proteins gave different amounts of nicked and linear products (FIGS. 5A-B). As shown in FIG. 5A, at 5 mM Mg$^{2+}$ and matched DNA, while the total activity at saturation was comparable between SpyCas9$^{WT}$ and SpyCas9$^{2Pro}$ (~70%), SpyCas9$^{WT}$ produced slightly more linear product (~65%), compared to that of SpyCas9$^{2Pro}$ (~54%), (FIG. 5A). With the mismatched MM5 substrate, SpyCas9$^{2Pro}$ (~20%) showed a clear reduction in the percentage of linear product as compared to SpyCas9$^{WT}$ (~60%), which accounted for the majority of the reduction in the total activity (FIG. 5B). Similar differences between SpyCas9$^{2Pro}$ and SpyCas9$^{WT}$ in the pattern of nicked and linear products were observed at 10 mM Mg$^{2+}$ for both matched and MM5 substrates (data not shown). The pattern stayed the same with sgRNA$^{FL}$ on both matched and MM5 substrates (data not shown), indicating that the reduction in linearization of mismatched DNA by SpyCas9$^{2Pro}$ is prevalent under the different conditions tested and does not change even in the presence of a full-length sgRNA. Interestingly, both SpyCas9$^{2Pro}$ and SpyCas9$^{WT}$ produce more nicked products with either matched or MM5 substrates at 1 mM Mg$^{2+}$, even though the absolute values are lower for SpyCas9$^{2Pro}$ in all the conditions that were tested (data not shown).

Expanding on the analyses of matched and MM5 substrates, we analyzed the amount of linear and nicked products produced by SpyCas9$^{WT}$ and SpyCas9$^{2Pro}$ with substrates containing mismatch(es) at various protospacer positions. Using data obtained at 50 nM enzyme complex, we computed $R_{L/N}$, the ratio of Linear vs. Nicked DNAs [equation (4)], for each replication, then averaged $R_{L/N}$ over three or more replications. At 5 mM Mg$^{2+}$, SpyCas9$^{WT}$ gave higher average $R_{L/N}$ values than SpyCas9$^{2Pro}$ for all 8 substrates tested. This shows that SpyCas9$^{2Pro}$ produces a lower relative fraction of linearized product compared to SpyCas9$^{WT}$, and therefore, is acting more like a "nickase". Reduction in linearizing activity of SpyCas9$^{2Pro}$ varies depending on the position of the mismatch.

For MM5 and MM7, two of the PAM-proximal single mismatch substrates that cause the most reduction in total cleavage by SpyCas9$^{2Pro}$ when compared to SpyCas9$^{WT}$ (FIGS. 1A-5B), the average $R_{L/N}$ of SpyCas9$^{2Pro}$ was reduced by about 8 times for MM5 and ~30 times for MM7 as compared to that of SpyCas9$^{WT}$. Further analyses showed that at 1 mM Mg$^{2+}$, SpyCas9$^{2Pro}$ had lower $R_{L/N}$ values for the matched and PAM-proximal mismatched substrates when compared to SpyCas9$^{WT}$, while the ratios are comparable for PAM-distal mismatches, except for MM18 that produced more linearization by SpyCas9$^{2Pro}$. The observations support the notion that BH-loop mutations cause a reduction in linearizing activity and that the effects are more pronounced at the PAM-proximal region.

Overall all, the pronounced nicking activity of SpyCas9$^{2Pro}$, especially on the mismatched DNA substrates, implies that the cleavage ability of one of the endonucleases is compromised in SpyCas9$^{2Pro}$ and that the impairment is more pronounced on target DNA with PAM-proximal mismatches.

Structural Flexibility of SpyCas9$^{WT}$ and SpyCas9$^{2Pro}$ Binary Complexes Varies.

As the BH-loop undergoes a loop-to-helix transition upon binding sgRNA and makes direct RNA contacts, the substitutions in the BH-loop likely affect the binary Cas9-sgRNA complex. EMSA measurements showed that at approximately 50 nM sgRNA$^{del}$, a 1:1 molar ratio of sgRNA and protein gave ~70% complex for SpyCas9$^{2Pro}$ and ~85% for SpyCas9$^{WT}$ (FIG. 6A). As such, under experimental conditions used to assess DNA cleavage (i.e., 50 nM equimolar protein and RNA, see FIGS. 2-4), the functional differences observed is not due to a significant reduction of sgRNA binding in SpyCas9$^{2Pro}$, but rather due to the structural and/or dynamic differences in the binary complex. This is also consistent with the observation that for matched DNA, SpyCas9$^{2Pro}$ and SpyCas9$^{WT}$ can cleave the precursor DNA to a comparable degree, albeit at a slower rate by SpyCas9$^{2Pro}$ (FIG. 3).

To further support the notion that differences exist between SpyCas9$^{WT}$ and SpyCas9$^{2Pro}$ in the binary protein-RNA complexes, we performed limited trypsin proteolysis. Comparing the apo-forms of SpyCas9$^{WT}$ and SpyCas9$^{2Pro}$, the banding pattern was similar for both proteins, except for an increase in the amount of a band in between 37 kDa and 50 kDa in SpyCas9$^{2Pro}$ (FIG. 6B, Band A). The binary complexes show different digestion patterns as compared to the apo-proteins, with more pronounced variations between SpyCas9$^{2Pro}$ and SpyCas9$^{WT}$ (FIG. 6B). SpyCas9$^{2Pro}$ protein bound to sgRNA (both deleted and full-length versions) is more easily degraded by trypsin compared to SpyCas9$^{WT}$ bound to sgRNA, as indicated by the reduction of the full-length SpyCas9$^{2Pro}$ compared to SpyCas9$^{WT}$ (FIG. 6B, Band B). In addition, another band in between 37 kDa and 50 kDa (FIG. 6B, Band C) is more intense in sgRNA bound SpyCas9$^{2Pro}$ as compared to that of SpyCas9$^{WT}$-sgRNA complex. These data indicate differences in the flexibility of the sgRNA-bound complexes of SpyCas9$^{2Pro}$ and SpyCas9$^{WT}$, which may lead to increased accessibility of trypsin to internal regions of SpyCas9$^{2Pro}$ and therefore loss of full-length protein. This implicates that the loop-to-helix transition of the BH and its interactions with sgRNA as observed in the crystal structures may be essential in organizing an efficient binary complex, although further work is required to reveal the details.

SpyCas9$^{2Pro}$ Shows Moderate Activity in Cell-Based Assays and Exhibit a Reduced Off-Target DNA Cleavage Compared to SpyCas9$^{WT}$.

We tested the ability of SpyCas9$^{2Pro}$ to produce lesions at seven different genomic sites of HEK293T cells using a TIDE assay. SpyCas9$^{2Pro}$ showed varying efficiencies in producing lesions on the seven target sites examined (FIG. 7A). One of the sites (DTS7) has comparable efficiencies for both proteins (68% lesion for SpyCas9$^{WT}$ and 42% for SpyCas9$^{2Pro}$) and another site (DTS55) has moderate cleavage efficiency in the case of SpyCas9$^{2Pro}$ (18%) compared to SpyCas9$^{WT}$ (65%) (FIG. 7A). At the rest of the five sites, the amount of lesions produced by SpyCas9$^{2Pro}$ is lower (varied between 1-3%) compared to SpyCas9$^{WT}$ (varied between 2-76%). There was no difference in the cleavage efficiency using a full length or a shorter version of sgRNA, similar to results observed in in vitro activity assays (FIG. 7B). Furthermore, while SpyCas9$^{WT}$ is not affected by a 20-nt or 21-nt guide region in the sgRNA construct, SpyCas9$^{2Pro}$ worked slightly more efficiently with a 20-nt guide region (FIG. 7B). The reduced efficiency of 21-nt gRNA to induce lesions has been previously observed for Cas9 variants developed for reduced off-targeting effect (High-fidelity Cas9, enhanced Cas9). The reduced targeting and cleavage efficiencies of SpyCas9$^{2Pro}$ indicates that the BH-loop is critical in a cellular environment compared to an in vitro setting where the reduction in total activity is not so pronounced especially while targeting a completely complementary DNA. It is possible that the BH-loop substitution is promoting more nicking under the cellular conditions, similar to in vitro assays. Since nicks can be efficiently repaired in a cellular environment[56], this can be translated into a reduction in the on-target DNA cleavage efficiency.

We proceeded to analyze the off-target effects of SpyCas9$^{2Pro}$. We compared the off-target editing profile following targeting of DTS7 genomic site of HEK293T cells by SpyCas9$^{WT}$ and SpyCas9$^{2Pro}$. We analyzed this by targeted deep sequencing of sites that have been previously shown as off-target sites for SpyCas9$^{WT}$ by GUIDE-seq. The results show an average on-target activity of 64% for SpyCas9$^{WT}$ and 39% for SpyCas9$^{2Pro}$. Interestingly, the off-target activity of SpyCas9$^{2Pro}$ was much lower compared to SpyCas9$^{WT}$ (FIG. 7C). SpyCas9$^{WT}$ produced significant levels of cleavage at two of the eight off-target areas that were tested (an average of 20% on site 1 and 12% on site 3). The amount of lesion produced by SpyCas9$^{2Pro}$ on site 1 is 3% and site 3 is 1%, and the rest of the sites averaged to 0% (data not shown). Thus, the specificity of DNA cleavage by SpyCas9$^{2Pro}$ that was manifested under in vitro conditions is translatable to cellular assays.

Discussion

SpyCas9$^{2Pro}$ Shows a Higher Degree of Selectivity in DNA Targeting.

The combined in vitro and cell-based analyses show that introducing two prolines in the BH-loop affects the DNA cleavage function of SpyCas9, with the effects being more pronounced in a cellular environment. In in vitro studies, SpyCas9$^{2Pro}$ shows significantly reduced total cleavage activities against targets with PAM-proximal mismatch(es) as compared to SpyCas9$^{WT}$(FIGS. 2A-4). The ability of SpyCas9$^{2Pro}$ to better discriminate against mismatched DNA is maintained in cellular assays as they demonstrate smaller degrees of off-target cleavage (FIG. 7C). Interestingly, in vitro analyses show that there is more nicked product formation by SpyCas9$^{2Pro}$ (FIGS. 5A-B), suggesting that the activity of one of the endonuclease sites, RuvC or HNH, is impacted in SpyCas9$^{2Pro}$ compared to SpyCas9$^{WT}$. In the cell-based assays, SpyCas9$^{2Pro}$ produces indels efficiently at only two out of the seven on-target sites tested (FIG. 7A). This is likely linked to the impairment of one of the endonuclease sites of SpyCas9$^{2Pro}$ that prevents double-stranded DNA breaks. Since nicked DNA can be repaired by the cellular machinery, deficiency of one of the nucleases' activity can lead to reduction in the number of indels produced. Previous work has shown that HypaCas9 variant acted on 19 out of the 24 endogenous sites tested, compared to 18 out of 24 in SpyCas9-HF1 and 23 out of 24 in eSpyCas9(1.1). This shows that substitutions in SpyCas9 affect the ability of the protein to act on different genomic sites perhaps due to weakened protein-nucleic acid interactions that in turn can potentially reduce off-target DNA cleavage. The reduction in on-target cleavage may be compounded in SpyCas9$^{2Pro}$ due to reduction in the linearization activity at the target sites. Overall, the data indicate that SpyCas9$^{2Pro}$ exhibits a higher degree of specificity in DNA targeting.

BH-Loop Substitution Potentially Affects Protein-RNA-DNA Interactions and Impacts Multiple Aspects of Cas9 Activity.

Our results show that the disruption of BH-loop affects more than one step in the catalytic cycle of Cas9. The BH-loop makes direct interactions with sgRNA and phosphate lock loop (PLL), yet SpyCas9$^{2Pro}$ and SpyCas9$^{WT}$ form a similar amount of binary protein-sgRNA complex (FIG. 6A). Interestingly, while SpyCas9$^{2Pro}$ can cleave matched DNA to a similar extent as compared to SpyCas9$^{WT}$ (FIGS. 1A-3), the rate of DNA cleavage is reduced in SpyCas9$^{2Pro}$ (data not shown). These results indicate that BH-loop disruption is not confined to a simple effect of RNA binding, but rather affects processes downstream of binary complex formation. Based on the available crystal structures and results reported here, we propose that proline substitutions in the BH-loop affect the conformational flexibility of Cas9-sgRNA binary complex, unwinding of DNA and stabilization of the nascent R-loop, and cross-talk between the two endonuclease sites. The reasonings are as follows.

The search of complementarity between a DNA target and the RNA guide is facilitated by a pre-organized seed region of the RNA guide in Cas9 and several protein-sgRNA interactions favor positioning of the seed region. For example, in both binary and ternary complexes of SpyCas9, the residues R63, R66, R70, R74, and R78 from the BH makes phosphate backbone interactions with the seed region (C18, G16, A15, G14 (PAM-proximal)) of the sgRNA. Substituting R66, R70, or R74 markedly reduces the activity of SpyCas9 and it was demonstrated that the interactions between the BH and the seed region of sgRNA are essential for R-loop initiation. The residue R66 lies in the BH-loop region and interacts with $14^{th}$ and $15^{th}$ nt in the seed region of the sgRNA through a direct H-bond. Water-mediated H-bonds are observed between R66 and the $62^{nd}$ and $63^{rd}$ nt of the tracrRNA in one of the SpyCas9 crystal structures (PDB ID: 4OO8). Even though R66 is not being directly substituted in the present study, the introduction of two consecutive prolines likely impacts helix formation in this region. This may affect positioning of R66 for interacting with sgRNA. It was previously shown that sgRNA without the seed sequence cannot induce conformational changes similar to that of sgRNA with the seed region, implicating that defects in organizing the seed region in SpyCas9$^{2Pro}$ could be translated to downstream conformational changes. We note that trypsin digestions indicate that the BH-loop substitutions alter the structure and dynamics of Cas9-sgRNA complex (FIG. 6B). However, further work is required to reveal the detailed changes in protein-RNA-DNA interactions in SpyCas9$^{2Pro}$ binary and ternary complexes.

In addition to the direct interaction of BH-loop with the sgRNA, BH-loop is indirectly involved in DNA unwinding. The PLL, which contacts the phosphate backbone of the DNA at +1 position to initiate strand switching of DNA for R-loop formation, interacts with the BH-loop. This interaction is through a H-bond between K65 of BH-loop and E1108 of PLL and this H-bond is maintained even in the binary complex (PDB-ID: 4ZT0), ready and poised for strand switching. In the present work, K65 has been substituted with a proline. The absence of this pre-organization can potentially affect DNA-unwinding in SpyCas9$^{2Pro}$.

The present work shows that SpyCas9$^{2Pro}$ has reduced activity with DNA substrates having PAM-proximal mismatches. The defects due to the absence of BH-loop conformational transition may be compensated at least partially by the strength of DNA-RNA base pairing along the initial regions of the guide region in a matched DNA target. It is reasonable to envisage that in the case of SpyCas9$^{2Pro}$ and target DNA with PAM-proximal mismatches, the compensatory RNA-DNA interactions are compromised. This may affect a productive R-loop formation, causing reduced activity with such DNA targets. For the PAM-distal mismatches, SpyCas9$^{2Pro}$ shows similar or slightly higher total activity as that of SpyCas9$^{WT}$. It has been reported that the pairing between 1 to ~14 nt in the RNA-DNA hybrid stabilizes the ternary complex and initiates HNH movement, with the HNH movement being modulated by mismatches at the PAM-distal end. The present data indicate that the BH-loop residues also play a subtle role in modulating the HNH movement.

SpyCas9$^{2Pro}$ demonstrated consistently more nicking with the different DNA substrates, especially with mismatches, compared to SpyCas9$^{WT}$. The coordination between HNH and RuvC by means of conformational changes to bring about double-strand DNA cleavage is well documented. The BH is directly linked to RuvC motif-II in the primary protein sequence. In addition, it was suggested based on molecular dynamics simulations that N844 and K848 of HNH can form interactions with E60 and T58 of BH. Cas9 substitutions affecting the positioning of endonuclease sites were previously observed in eSpyCas9(1.1) and SpyCas9-HF1. In eSpyCas9(1.1) and SpyCas9-HF1, HNH is trapped in an intermediate, inactive state when they bind to mismatched DNA targets, and since the positioning of HNH is important for RuvC activity, the off-target DNA cleavage is reduced in these Cas9 variants. Interestingly, it was shown that mismatches between crRNA and protospacer can promote formation of nonproductive protein-RNA complex that causes accumulation of DNA nicks. These previous studies and the present data support our hypothesis that the communication between the endonuclease sites is impaired in SpyCas9$^{2Pro}$ and that the effect is more pronounced when SpyCas9$^{2Pro}$ binds to mismatched targets, thus reducing DNA linearization.

Gene-Editing Capabilities of SpyCas9$^{2Pro}$.

The cell-based analysis shows that SpyCas9$^{2Pro}$ is not comparable to SpyCas9$^{WT}$ in its gene-editing capabilities. The impairment of the cross-talk between the endonuclease domains may be the strong contributor for this, since nicks are efficiently repaired in a cellular environment. Interestingly, Cas9 "nickase" has been shown as a strategy to reduce off-target effects. It might be possible to improve the on-target activity of SpyCas9$^{2Pro}$ using two sgRNAs to nick individual strands within a target genomic site. Similarly, the BH-loop substitutions can be tested along with other high-efficient Cas9 variants to analyze the presence of synergistic effects.

Cas9 Utilizes Structuring of ARM Region in Response to RNA-Binding as Found in Other RNA Binding Proteins.

ARM is an RNA-binding motif that comprises around 8-10 amino acids, usually enriched in basic amino acids, especially arginine. The ARM motif is able to recognize and bind specific RNA structural elements such as stem loop or bulge regions. The ARM regions in several RNA-binding proteins have been shown to be disordered or with lower helical content in the apo-form, with an increase in the helical content after binding to specific RNA. ARM can adopt different protein structural elements such as beta hairpins, alpha helix, and random coils after binding specific RNA targets.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the present disclosure.

What is claimed is:

1. A variant of *Streptococcus pyogenes* Cas9 (SpyCas9) protein, comprising: a nuclease (NUC) lobe, a recognition (REC) lobe, and a modified bridge helix (BH) region joining the NUC lobe and the REC lobe, the variant SpyCas9 protein having increased DNA cleavage selectivity relative to a corresponding wild type SpyCas9 protein, and wherein the variant SpyCas9 protein has at least 90% identity to the amino acid sequence of SEQ ID NO:1, and comprises a proline substitution in at least one of amino acid positions L64 and K65 as numbered compared to SEQ ID NO: 1, or one or more amino acid positions 49 and 50, wherein the amino acid positions 49 and 50 are numbered relative to *Staphylococcus aureus* Cas9 (SauCas9) protein set forth in SEQ ID NO: 2.

2. The variant SpyCas9 protein of claim 1, wherein the amino acid positions L64 and K65 are both substituted.

3. The variant SpyCas9 protein of claim 1, wherein the amino acid positions L64 and K65 are both substituted with proline.

4. The variant SpyCas9 protein of claim 1, having at least 95% identity to the amino acid sequence of SEQ ID NO: 1.

5. A system comprising the variant SpyCas9 protein of claim 1, and a SpyCas9 guide RNA.

6. A method of gene editing, comprising using a variant *Streptococcus pyogenes* Cas9 (SpyCas9) protein of claim 1 in a CRISPR-Cas gene-editing procedure, wherein the variant SpyCas9 protein comprises a nuclease (NUC) lobe, a recognition (REC) lobe, and a modified bridge helix (BH) region joining the NUC lobe and the REC lobe, and wherein the variant SpyCas9 protein has increased DNA cleavage selectivity relative to a corresponding wild type SpyCas9 protein and has at least 90% identity to the amino acid sequence of SEQ ID NO:1, and comprises a proline substitution in at least one of amino acid positions L64 and K65 as numbered compared to SEQ ID NO: 1, or one or more of amino acid positions 49 and 50, wherein the amino acid positions 49 and 50 are numbered relative to *Staphylococcus aureus* Cas9 (SauCas9) protein set forth in SEQ ID NO: 2.

7. The method of claim 6, wherein the amino acid positions L64 and K65 are both substituted.

8. The method of claim 6, wherein the amino acid positions L64 and K65 are both substituted with proline.

9. The method of claim 6, wherein the variant SpyCas9 protein has at least 95% identity to the amino acid sequence of SEQ ID NO: 1.

* * * * *